(12) United States Patent
Golden et al.

(10) Patent No.: US 9,492,303 B2
(45) Date of Patent: Nov. 15, 2016

(54) SHOULDER IMMOBILIZER AND FRACTURE STABILIZATION DEVICE

(75) Inventors: Steve Golden, Menlo Park, CA (US);
Nathaniel Cohen, Los Gatos, CA (US);
(Continued)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 13/473,531

(22) Filed: May 16, 2012

(65) Prior Publication Data
US 2013/0131568 A1 May 23, 2013

Related U.S. Application Data

(63) Continuation of application No. PCT/US2010/057286, filed on Nov. 18, 2010.
(Continued)

(51) Int. Cl.
*A61F 5/02* (2006.01)
*A41D 27/26* (2006.01)
(Continued)

(52) U.S. Cl.
CPC ............... *A61F 5/013* (2013.01); *A41D 13/00* (2013.01); *A41D 13/05* (2013.01);
(Continued)

(58) Field of Classification Search
CPC ............... A61F 5/00; A61F 5/01; A61F 5/37; A61F 5/3715; A61F 5/3723; A61F
(Continued)

(56) References Cited

U.S. PATENT DOCUMENTS

| 2,310,556 A | 2/1943 | Anderson |
| 2,704,069 A | 3/1955 | Donelan |

(Continued)

FOREIGN PATENT DOCUMENTS

| CA | 2041903 | 12/1997 |
| DE | 20 2005 002 610 U1 | 8/2005 |

(Continued)

OTHER PUBLICATIONS

Canale, S. Terry and James H. Beaty, *Campbell's operative orthopaedics*, 11$^{th}$ Edition. Philadelphia, Pennsylvania, Mosby, Inc., 2008. pp. 2694-2695.
(Continued)

*Primary Examiner* — Justine Yu
*Assistant Examiner* — Brandon L Jackson
(74) *Attorney, Agent, or Firm* — EIP US LLP

(57) ABSTRACT

A shoulder immobilizer (20) includes a semi-rigid or rigid orthosis, in the form of an arm support (22), which supports the upper arm, elbow, forearm and wrist of a patient. A bolster (24) is positioned between the patient and the arm support (22). A body strap (26) extends around the patient and attaches to the arm support (22) and/or the bolster (24), holding the arm support and bolster in position against the body of the patient. In embodiments, the shoulder immobilizer (20) may utilize a shoulder strap (28), but such a shoulder strap is not necessary for shoulder immobilization of the patient.

1 Claim, 19 Drawing Sheets

(75) Inventors: Ronald Joseph, Saratoga, CA (US);
Marc Safran, Stanford, CA (US)

Related U.S. Application Data

(60) Provisional application No. 61/262,503, filed on Nov. 18, 2009, provisional application No. 61/297,001, filed on Jan. 21, 2010.

(51) Int. Cl.

| | |
|---|---|
| *A61F 5/37* | (2006.01) |
| *A61F 13/00* | (2006.01) |
| *A61B 19/00* | (2006.01) |
| *A61F 13/06* | (2006.01) |
| *A61F 5/00* | (2006.01) |
| *A61F 5/01* | (2006.01) |
| *A41D 13/05* | (2006.01) |
| *A41D 13/00* | (2006.01) |
| *A61F 5/05* | (2006.01) |
| *A41D 13/08* | (2006.01) |
| *A61F 5/058* | (2006.01) |
| *A61F 5/04* | (2006.01) |
| *A61F 7/00* | (2006.01) |

(52) U.S. Cl.
CPC ........... *A41D 13/0512* (2013.01); *A41D 13/08* (2013.01); *A61F 5/00* (2013.01); *A61F 5/01* (2013.01); *A61F 5/0118* (2013.01); *A61F 5/04* (2013.01); *A61F 5/05* (2013.01); *A61F 5/05841* (2013.01); *A61F 5/05858* (2013.01); *A61F 5/37* (2013.01); *A61F 5/373* (2013.01); *A61F 5/3715* (2013.01); *A61F 5/3738* (2013.01); *A61F 5/3746* (2013.01); *A61F 5/3753* (2013.01); *A61F 7/00* (2013.01)

(58) Field of Classification Search
CPC ................. 5/373;A61F 5/3738; A61F 5/0118; A61F 5/04; A61F 5/05; A61F 5/05841; A61F 5/05858; A61F 5/05866; A61F 5/3746; A61F 7/00; A61F 207/0001; A61F 2007/0029; A61F 2007/003; A61F 2007/0031; A61F 2007/0032; A61F 2007/0035; A41D 13/00; A41D 13/05; A41D 13/0512; A41D 13/08
USPC ...................... 5/623, 646; 128/846, 869, 876, 128/878–881, 892; 602/4, 5, 12, 2, 20–22; 2/44–45, 459
See application file for complete search history.

(56) References Cited

U.S. PATENT DOCUMENTS

| | | | |
|---|---|---|---|
| 3,103,216 A | 9/1963 | Scott | |
| 3,404,680 A | 10/1968 | Guttmann et. al. | |
| 3,788,308 A | 1/1974 | Simpson | |
| 4,180,870 A | 1/1980 | Radulovic et al. | |
| 4,198,964 A | 4/1980 | Honneffer | |
| 4,220,149 A | 9/1980 | Mims, Jr. | |
| 4,232,664 A | 11/1980 | Blatt | |
| 4,372,301 A | 2/1983 | Hubbard et al. | |
| 4,437,459 A | 3/1984 | Slavetskas | |
| 4,480,637 A | 11/1984 | Florek | |
| 4,489,716 A | 12/1984 | Blackwood et al. | |
| 4,497,316 A | 2/1985 | Lilla | |
| 4,564,008 A | 1/1986 | Donahoo | |
| 4,572,172 A | 2/1986 | Williams | |
| 4,598,701 A | 7/1986 | Schaefer | |
| 4,617,923 A | 10/1986 | Coleman | |
| 4,622,961 A | 11/1986 | Christensen | |
| 4,625,719 A | 12/1986 | Chambers | |
| 4,716,895 A | 1/1988 | Marques et al. | |
| 4,759,353 A | 7/1988 | Melendez et al. | |
| 4,805,620 A * | 2/1989 | Meistrell | 607/112 |
| 4,834,082 A | 5/1989 | Ghadiali | |
| 4,896,660 A | 1/1990 | Scott | |
| 4,910,818 A | 3/1990 | Grabill | |
| D317,840 S | 7/1991 | Jagdat | |
| 5,334,132 A | 8/1994 | Burkhead | |
| 5,337,737 A * | 8/1994 | Rubin et al. | 601/33 |
| 5,383,844 A | 1/1995 | Munoz et al. | |
| 5,385,536 A | 1/1995 | Burkhead et al. | |
| 5,407,420 A | 4/1995 | Bastyr et al. | |
| 5,407,430 A | 4/1995 | Peters | |
| 5,413,552 A | 5/1995 | Iwuala | |
| 5,423,333 A | 6/1995 | Jensen et al. | |
| RE35,028 E | 8/1995 | Casebolt et al. | |
| 5,464,383 A | 11/1995 | Padden et al. | |
| 5,509,426 A | 4/1996 | Sowerby | |
| 5,569,172 A | 10/1996 | Padden et al. | |
| 5,665,058 A | 9/1997 | Young | |
| 5,716,334 A | 2/1998 | Wade | |
| 5,772,617 A | 6/1998 | Lay | |
| D396,291 S | 7/1998 | Bakes | |
| 5,792,083 A | 8/1998 | Joslin | |
| 5,830,165 A | 11/1998 | Rowe et al. | |
| 5,941,263 A | 8/1999 | Bierman | |
| 6,007,500 A | 12/1999 | Quintinskie | |
| 6,095,993 A | 8/2000 | Hawkins | |
| 6,099,489 A | 8/2000 | Herzberg et al. | |
| 6,102,877 A | 8/2000 | Joslin | |
| 6,113,562 A | 9/2000 | Bonutti et al. | |
| 6,221,037 B1 | 4/2001 | Johnson et al. | |
| 6,533,741 B1 | 3/2003 | Lee et al. | |
| 6,595,937 B1 | 7/2003 | Moon et al. | |
| 6,659,971 B2 | 12/2003 | Gaylord | |
| 6,691,353 B2 | 2/2004 | Fuhriman | |
| 6,770,044 B1 | 8/2004 | Joslin | |
| 6,932,781 B2 | 8/2005 | Itoi | |
| 7,189,213 B1 | 3/2007 | Weber | |
| 7,244,239 B2 | 7/2007 | Howard | |
| 7,300,410 B1 | 11/2007 | Weber | |
| 7,441,293 B1 | 10/2008 | Singer et al. | |
| 7,563,236 B2 | 7/2009 | Kazmierczak et al. | |
| D598,116 S | 8/2009 | Vollbrecht | |
| 7,634,828 B2 | 12/2009 | Elhabashy | |
| 7,749,179 B2 | 7/2010 | Hargrave et al. | |
| 2003/0135141 A1 | 7/2003 | Berhorst | |
| 2003/0187373 A1 | 10/2003 | Gaylord | |
| 2004/0129278 A1* | 7/2004 | Itoi | 128/892 |
| 2005/0010147 A1 | 1/2005 | Kazmierczak et al. | |
| 2005/0020950 A1 | 1/2005 | Jestrabek-Hart | |
| 2005/0080369 A1* | 4/2005 | Kim | A61F 5/05858 602/12 |
| 2005/0234375 A1 | 10/2005 | Grim et al. | |
| 2007/0100266 A1 | 5/2007 | Hargrave et al. | |
| 2010/0121236 A1 | 5/2010 | Goumas | |

FOREIGN PATENT DOCUMENTS

| | | |
|---|---|---|
| EP | 0 362 528 A1 | 4/1990 |
| EP | 0904752 | 3/1999 |
| EP | 1 645 251 A2 | 4/2006 |
| FR | 2 589 722 A1 | 5/1987 |
| FR | 2 619 307 A1 | 2/1989 |
| FR | 2771625 | 6/1999 |
| GB | 2 441 742 A | 3/2008 |
| JP | 2001-299789 | 10/2001 |
| WO | 86/03399 A1 | 6/1986 |

OTHER PUBLICATIONS

Corflex, Inc. "Ultra Cubital Tunnel Splint." [online], [retrieved on Sep. 25, 2006]. Retrieved from the Internet: <URL: http://www.corflex.com/>.
International Search Report and Written Opinon mailed Jan. 31, 2011 in Application No. PCT/US10/57286 filed Nov. 18, 2010.
ltoi et al., "Position of Immobilization After Dislocation of the Glenohumeral Joint, The Journal of Bone and Joint Surgery", May 2001, pp. 661-667, vol. 83-A, No. 5.

(56) References Cited

OTHER PUBLICATIONS

Breg, Inc., Product Brochure, Neutral Wedge, date unknown, 2 pages.
Scott Kober, Upper Extremity—Patients Immobilized in External Rotation Avoid Recurrent Dislocations, Orthopedics Today—On-line Newspaper, Mar. 2003, 3 pages.
Upper Extremity Bracing depicting the Slingshot, Adjustable Sling and Shoulder Abduction Pillow, Breg © Product Catalog 2002, 1 page.
DonJoy Shoulder Stabilizer Developed with Dr. Tom Sawa, DonJoyTM advertisement, 2 pages (front and back), Feb. 2002.
Quadrant by DonJoy shoulder brace, Smith & Nephew DonJoy, Inc. catalog, 2 pages, Mar. 1995.
Humeral Stabilizing System, Smith & Nephew DonJoy, Inc. catalog, 2 pages, Mar. 1992.
The S.C.O.I. Shoulder Brace, Smith & Nephew DonJoy, Inc. catalog, 1 page, Jun. 1990.

* cited by examiner

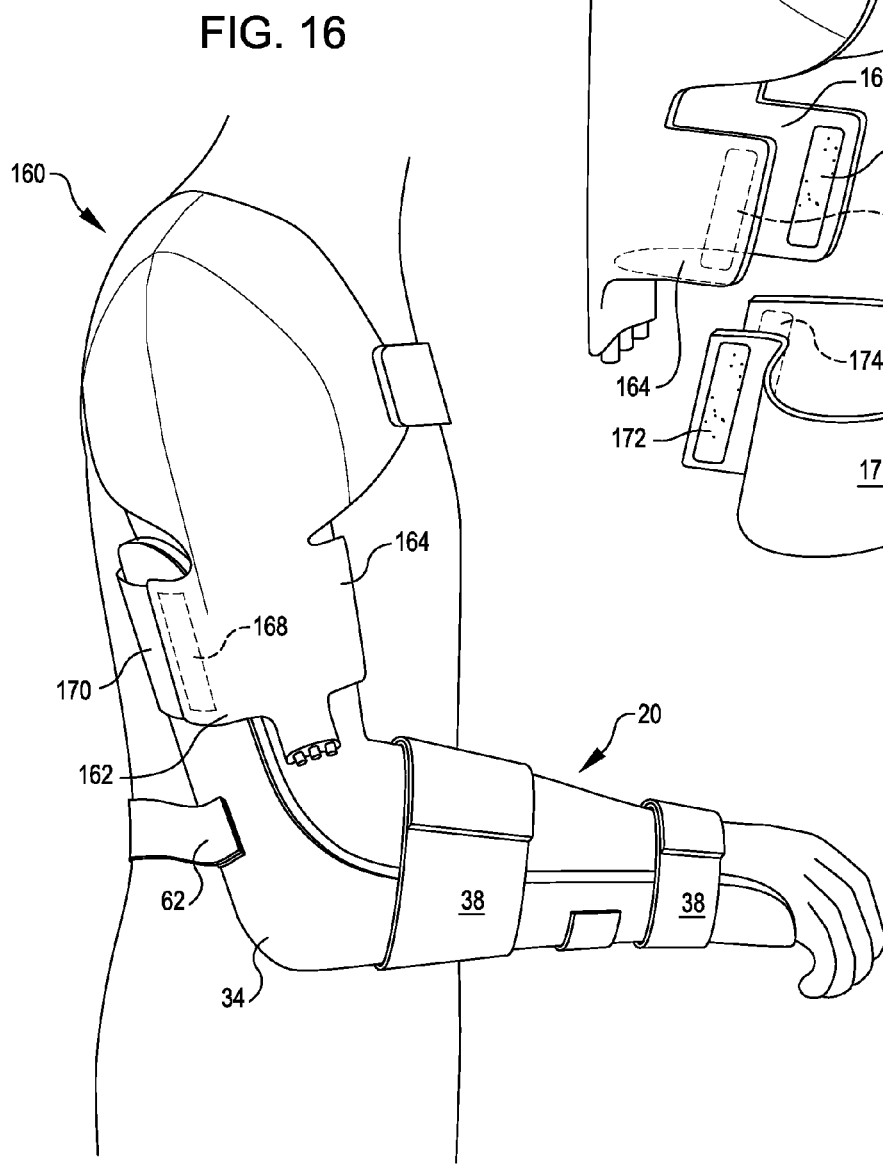
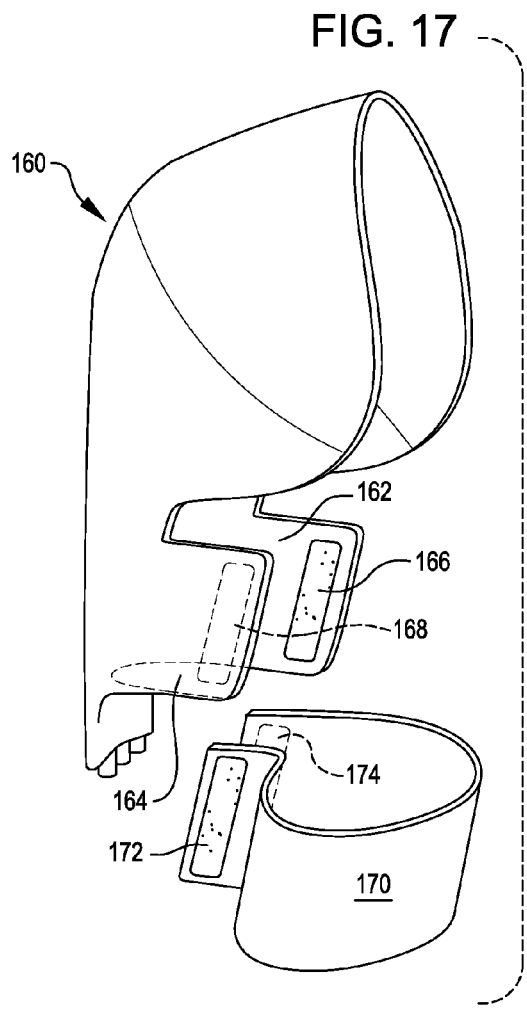

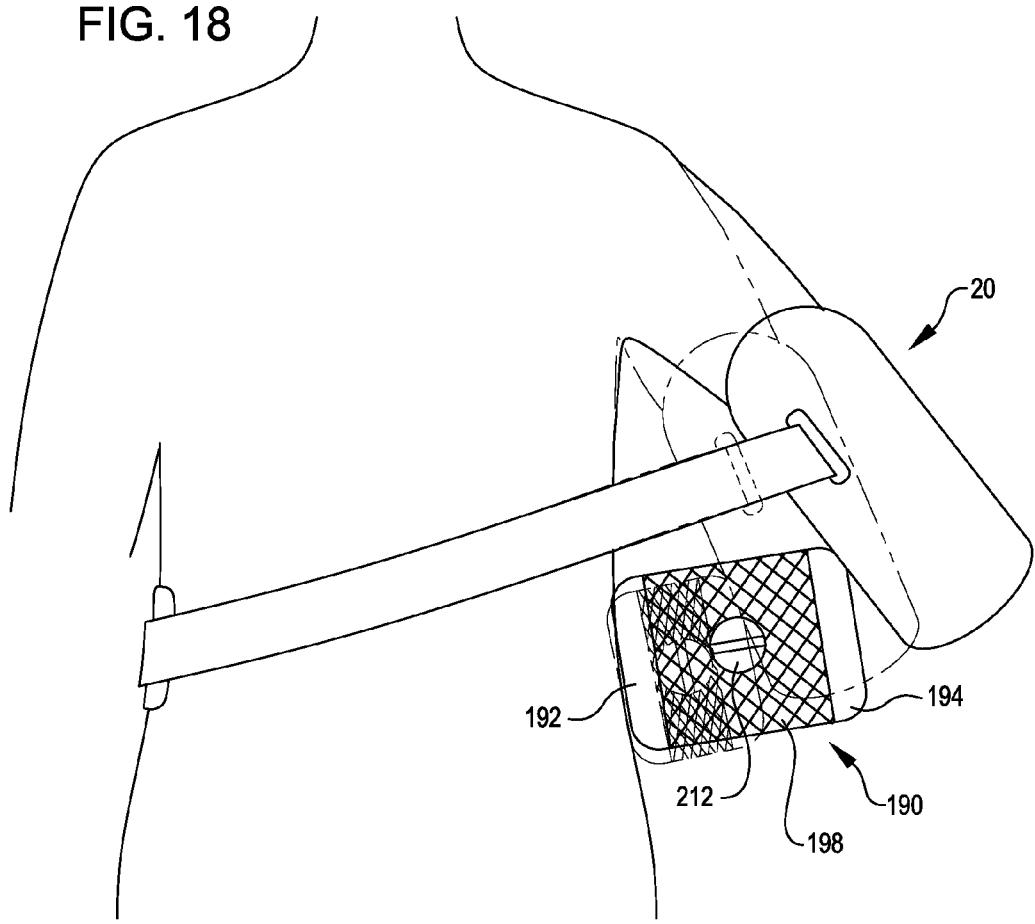

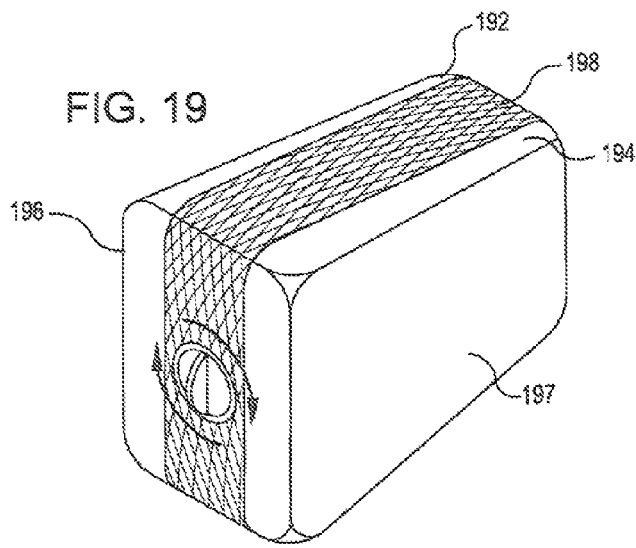
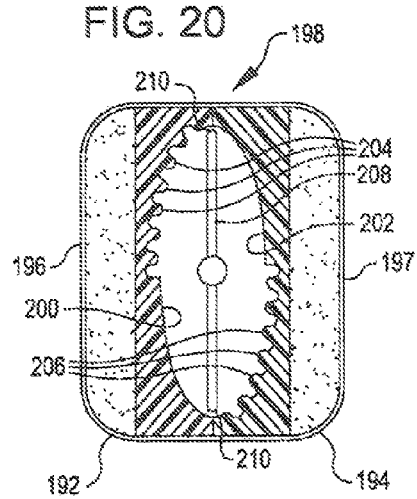
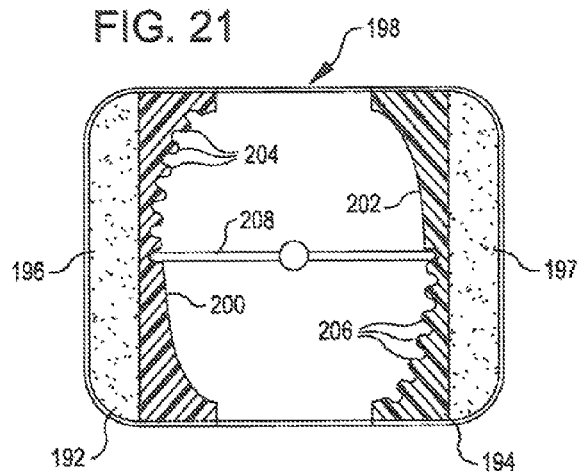

SHOULDER IMMOBILIZER AND FRACTURE STABILIZATION DEVICE

CROSS-REFERENCES TO RELATED APPLICATIONS

This application is a continuation of PCT Application No. PCT/US2010/057286, filed Nov. 18, 2010, which application claims the benefit of U.S. Provisional Application No. 61/262,503, filed on Nov. 18, 2009; and U.S. Provisional Application No. 61/297,001, filed on Jan. 21, 2010, the full disclosures of which are incorporated herein by reference.

BACKGROUND

Shoulder immobilizers are used to immobilize an injured or post-operative shoulder. Such immobilizers may be used, for example, after fractures or rotator cuff repair. Many of these devices utilize a neck strap for support, which can be very uncomfortable.

Some existing shoulder immobilizers utilize a fabric pouch attached to a bulky foam bolster. The bolster is positioned between the wearer's elbow and body. Such pouch/bolster designs easily move around a patient and do not provide adequate support or stabilization, especially while sleeping, which results in slower healing and pain. Other prior art immobilizers that do provide support are cumbersome and very restrictive and don't allow the patient to participate in daily or work activities, such as computer use or holding a cup of coffee.

Description of the Background Art

The following references may describe relevant background art: U.S. Patent Application No. 2005234375; U.S. Pat. Nos. 6,533,741; 5,665,058; 5,509,426; 5,407,420; 4,489,716; 2,704,069; 6,221,037; 4,232,664; 6,595,937; 5,941,263; 5,464,383; 4,598,701; 4,896,660; 6,932,781; 7,563,236; 7,244,239; D598,116; 7,300,410; 7,189,213; 6,659,971; 4,497,316; 4,572,172; 6,691,353; 4,716,895; German Patent No. DE202005002610U1; French Patent Nos. FR2589722A1; FR2619307A1; Great Britain Patent No. GB2441742A; European Patent Office Nos. EP362528A1; EP1645251A2; and World Intellectual Patent Office No. WO1986003399A1.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In embodiments, a shoulder immobilizer is provided, including a rigid or semi-rigid arm support, comprising a lower forearm support comprising a first surface for receiving a forearm of the patient and supporting the forearm in a substantially horizontal position when in use; and an upper arm support for extending along a back portion of the patient's arm when worn by a patient, the upper arm support comprising a second surface for extending against the back of the upper arm, the upper arm support extending at an angle to perpendicular when the forearm of the patient is in the forearm support and the upper arm support is against the back of the upper arm of the patient, the angle directing the elbow of a patient into a position of abduction relative to the patient's side. A bolster is provided for positioning between the arm support and the side of a patient, the bolster spacing the elbow of the patient away from the patient at the angle.

In embodiments, the bolster is connected to the arm support, and may be releasably connected to the arm support, for example by hook and loop fasteners.

A body strap may be provided for extending about a torso of a patient and attaching to the arm support to hold the arm support and bolster in place against the patient. In embodiments, when installed on a patient, the body strap connects to the upper arm support, extends around the torso of the patient, and attaches to the lower forearm support.

A shoulder strap may be connected to the arm support and designed, when the shoulder immobilizer is installed on a patient, to extend over the opposite side of the head of the patient and on the shoulder of the patient.

The bolster may include an anterior lobe that, when the shoulder immobilizer is installed on a patient, extends against an anterior portion of the patient and resists internal rotation of the forearm of the patient.

The angle may be greater than 0 degrees and less than 30 degrees, preferably between approximately 10 and 15 degrees, and more preferably approximately 10 degrees.

In embodiments, the first surface comprises a concave, upwardly-facing receiving surface, and/or the second surface comprises an elongate, concave receiving surface.

In embodiments, a shoulder immobilizer is provided, including a rigid or semi-rigid arm support, comprising a lower forearm support extending outward when the shoulder immobilizer is worn by a patient, the forearm support comprising a receiving surface for receiving a forearm of the patient and supporting the forearm in a substantially horizontal position when in use; an upper arm support for extending along a back portion of the patient's arm when worn by a patient; and a bolster for positioning between the arm support and the side of a patient, the bolster spacing the elbow of the patient away from the patient and comprising an anterior lobe that, when the shoulder immobilizer is installed on a patient, extends against an anterior of the patient and resists internal rotation of the forearm of the patient.

In embodiments, the bolster is connected to the arm support, and may be releasably connected to the arm support, for example by hook and loop fasteners.

In embodiments, the bolster includes a nonslip surface for contacting the patient's body.

A body strap may be provided for extending about a torso of a patient and attaching to the arm support to hold the arm support and bolster in place against the patient. In embodiments, when installed on a patient, the body strap connects to the upper arm support, extends around the torso of the patient, and attaches to the lower forearm support.

In additional embodiments, a shoulder immobilizer is provided, including a rigid or semi-rigid arm support, having a lower forearm support extending outward when the shoulder immobilizer is worn by a patient, the forearm support comprising a receiving surface for receiving a forearm of the patient and supporting the forearm in a substantially horizontal position when in use; an upper arm support for extending along a back portion of the patient's arm when worn by a patient; and a posterior cushion connected to a posterior of the upper arm support and configured to raise an elbow of the patient more than a shoulder of the patient when the patient is lying on the patient's back.

In embodiments, the posterior cushion tapers downward in thickness from an elbow region of the patient to a shoulder region of the patient.

The posterior cushion may be releasably attached to the arm support, for example, by hook and loop fasteners.

Embodiments include a bolster for positioning between the arm support and the side of a patient, the bolster spacing the elbow of the patient away from the patient. The bolster may be connected to the arm support.

A body strap may be provided for extending about a torso of a patient and attaching to the arm support to hold the arm support and bolster in place against the patient. In embodiments, when installed on a patient, the body strap connects to the upper arm support, extends around the torso of the patient, and attaches to the lower forearm support.

In further embodiments, a shoulder immobilizer is provided including a rigid or semi-rigid arm support, comprising a lower forearm support extending outward when the shoulder immobilizer is worn by a patient, the forearm support comprising a receiving surface for receiving a forearm of the patient and supporting the forearm in a substantially horizontal position when in use; an upper arm support for extending along a back portion of the patient's arm when worn by a patient; and a support cushion configured to engage the lower forearm support and a surface when a patient is wearing the shoulder immobilizer and the patient is lying on the patient's side on the surface.

In embodiments, the support cushion is configured to contact an anterior of the patient while engaging the lower forearm support and the surface.

The support cushion may be releasably connected to the arm support, for example, attached by hook and loop fasteners.

In embodiments, a bolster for positioning between the arm support and the side of a patient, the bolster spacing the elbow of the patient away from the patient. The bolster may be connected to the arm support.

A body strap may be provided for extending about a torso of a patient and attaching to the arm support to hold the arm support and bolster in place against the patient. When installed on a patient, the body strap may connect to the upper arm support, extends around the torso of the patient, and attaches to the lower forearm support.

In still further embodiments, a shoulder immobilizer is provided including a rigid or semi-rigid arm support, comprising a lower forearm support extending outward when the shoulder immobilizer is worn by a patient, the forearm support comprising a receiving surface for receiving a forearm of the patient and supporting the forearm in a substantially horizontal position when in use; and an upper arm support for extending along a back portion of the patient's arm when worn by a patient; and the lower forearm support being configured and arranged such that, when a patient is wearing the shoulder immobilizer and the back portion of the patient's upper arm is against the upper arm support, at least a portion of the palm of the patient is supported against the lower forearm support.

In embodiments, the wrist is supported by the forearm support in a positioned for typing. A wrist pad may be provided for supporting the wrist.

In still further embodiments, a shoulder immobilizer is provided, including a rigid or semi-rigid arm support, comprising a lower forearm support extending outward when the shoulder immobilizer is worn by a patient, the forearm support comprising a receiving surface for receiving a forearm of the patient and supporting the forearm in a substantially horizontal position when in use; and an upper arm support for extending along a back portion of the patient's arm when worn by a patient. A bolster is also provided for positioning between the arm support and the side of a patient; and an elastic body strap for extending about a torso of a patient and attaching to at least one of the arm support and the bolster to hold the arm support and bolster in place against the patient.

In embodiments, when installed on a patient, the elastic body strap connects to the upper arm support, extends around the torso of the patient, and attaches to the lower forearm support.

In yet further embodiments, a shoulder immobilizer is provided, including a rigid or semi-rigid arm support, comprising a lower forearm support extending outward when the shoulder immobilizer is worn by a patient, the forearm support comprising a concave, upwardly-facing receiving surface for receiving a forearm of the patient and supporting the forearm in a substantially horizontal position when in use; an upper arm support for extending along a back portion of the patients arm when worn by a patient, the upper arm support comprising a concave surface for receiving the back of the upper arm; and straps for connecting the arm of a patient into the arm support. When the shoulder immobilizer is worn by a patient, the arm of the patient in the arm support is openly exposed at an upper portion of the lower forearm support and in an anterior portion of the upper arm support.

In embodiments, a bolster for positioning between the arm support and the side of a patient is provided, the bolster spacing the elbow of the patient away from the patient. A body strap may be provided for extending about a torso of a patient and attaching to at least one of the arm support and the bolster to hold the arm support and bolster in place against the patient.

In embodiments, a shoulder immobilizer, including a rigid or semi-rigid arm support, comprising a lower forearm support extending outward when the shoulder immobilizer is worn by a patient, the forearm support for receiving a forearm of the patient and supporting the forearm in a substantially horizontal position when in use; and an upper arm support for extending along a back portion of the patients arm when worn by a patient, the upper arm support for receiving the back of the upper arm. A bolster is provided for positioning between the arm support and the side of a patient, the bolster spacing the elbow of the patient away from the patient's torso, and a body strap for extending about a torso of a patient and attaching to at least one of the arm support and the bolster to hold the arm support and bolster in place against the patient. The body strap, the bolster, and the arm support immobilizing a patient's shoulder independent of use of a shoulder strap.

In an embodiment, a shoulder immobilizer is provided, including a rigid or semi-rigid arm support, comprising a lower forearm support extending outward when the shoulder immobilizer is worn by a patient, the forearm support comprising a receiving surface for receiving a forearm of the patient and supporting the forearm in a substantially horizontal position when in use; an upper arm support for extending along a back portion of the patient's arm when worn by a patient; straps for attaching to opposite sides of the arm support; and wherein the arm support and the straps are arrangeable to receive a left or right arm of a patient; and a bolster for positioning between the arm support and the side of a patient, the bolster spacing the elbow of the patient away from the patient. A body strap may be provided for extending about a torso of a patient and attaching to the arm support to hold the arm support and bolster in place against the patient.

For a fuller understanding of the nature and advantages of the present invention, reference should be made to the ensuing detailed description and accompanying drawings.

BRIEF DESCRIPTION OF THE DRAWINGS

FIGS. 16 and 17 show a butterfly style cold therapy unit that may be utilized with a shoulder immobilizer in accordance with additional embodiments;

FIG. 18 shows a bolster that may be adjustable in width so as to vary the abduction angle of an immobilized arm in accordance with embodiments;

FIGS. 19, 20, and 21 show an expandable bolster in accordance with an embodiment;

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
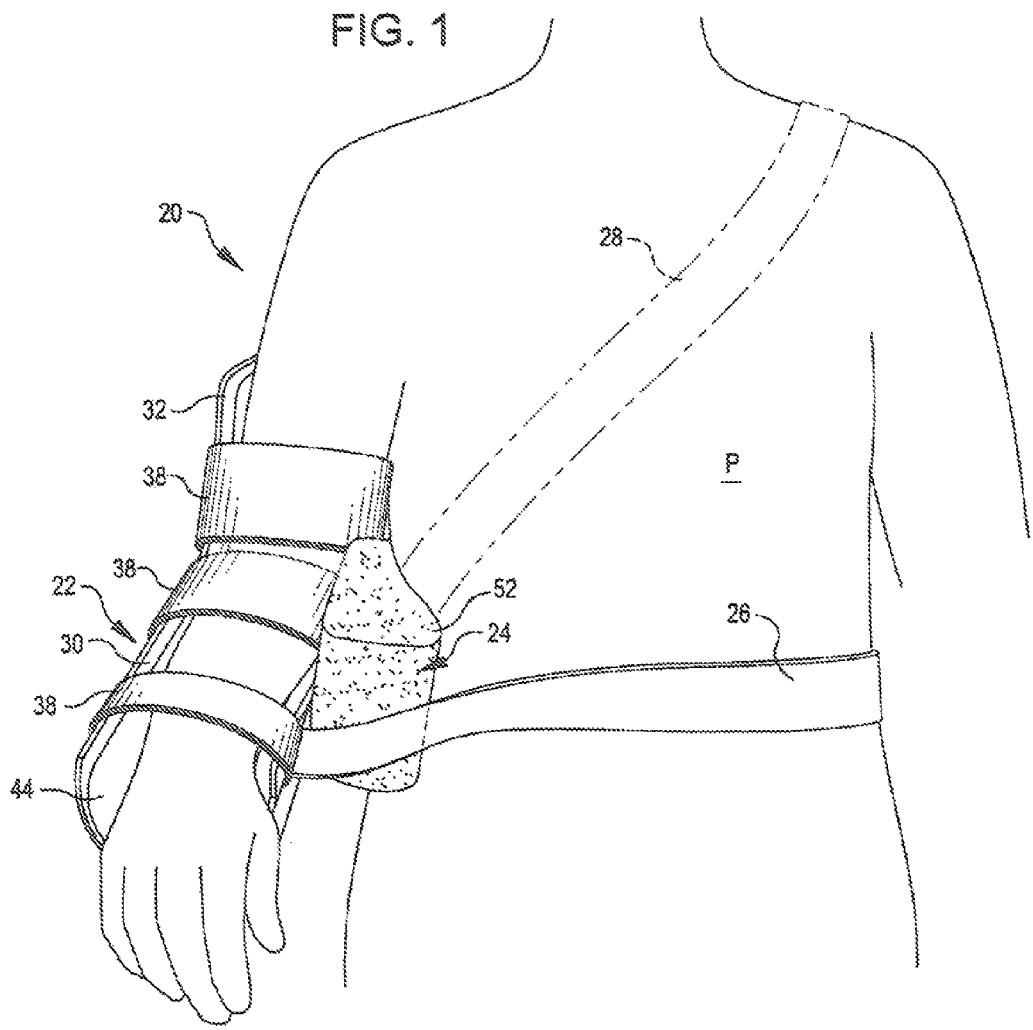
FIG. 1 is a perspective view of a shoulder immobilizer installed on a patient in accordance with an embodiment.

Referring now to the drawings, in which like reference numerals represent like parts throughout the several views, FIG. 1 is a perspective view of a shoulder immobilizer 20 installed on a patient P in accordance with an embodiment. In general, a shoulder immobilizer is designed to stabilize a patient's shoulder after an injury and/or in a post-operative period following reconstructive surgery. In embodiments herein, the shoulder immobilizer 20 is a system that allows support and immobilization of the shoulder during daily activities and for sleep.

Generally described, in the embodiments shown in the drawings, the shoulder immobilizer 20 includes a semi-rigid or rigid orthosis, in the form of an L-shaped arm support 22, which supports the upper arm, elbow, forearm and wrist of a patient. By L-shaped, we mean that the arm support bends at the elbow, but not necessarily at 90 degrees. In fact, the angle of bend could be less than or greater than 90 degrees, or could be adjustable, as described below. The arm support 22 provides a permanent state of flexion and is supported in a fixed position against the body. Thus, the arm support 22 provides cantilevered support for the wrist and distal portion of the forearm of the patient P. A bolster 24 is positioned between the patient and the arm support 22. A body strap 26 extends around the patient and attaches to the arm support 22 and/or the bolster 24, holding the arm support 22 and bolster 24 in position against the body of the patient P. In embodiments, the shoulder immobilizer 20 may utilize a neck or shoulder strap 28, but as described below, such a shoulder strap is not necessary for shoulder immobilization of the patient P, and in fact immobilization without a shoulder strap is a feature provided by embodiments described herein. As used herein, a "shoulder strap" may be a neck strap or other strap that extends over the shoulder of a patient.

In embodiments, the arm support 22 is formed of a rigid or semi-rigid material, such as plastic, a composite, metal, wood, or another suitable material or composition. The arm support 22 in the drawings includes a lower forearm portion 30, for example shown in FIG. 2, that supports a forearm of the patient P in use, preferably in a horizontal direction when the patient P is sitting or standing. In the embodiments shown in the drawings, the lower forearm portion 30 is shaped as a concave channel extending the length of the lower forearm portion. However, other structures may be provided, and the overall shape may be curved, flat, or contoured, and may include side restraints, such as tabs or walls, or other suitable features for extending and supporting the forearm in a desired position. In embodiments, when the arm support 22 is in place and the patient is upright, the lower forearm portion 30 extends in a substantially horizontal manner, fully supporting the forearm in a horizontal position.

An upper arm portion 32 is attached to the lower forearm portion 30 at an elbow 34. The upper arm portion 32 is designed to extend against the upper arm of a patient, such as the patient P. In the embodiments shown in the drawings, the upper arm portion 32 includes a concave channel extending its length, but other structures may be provided, as described above with respect to the lower forearm portion 30. In embodiments, the lower forearm portion 30 and upper arm portion 32 extend at a flexion angle to each other so as to provide support for the shoulder of the patient. As an example, the arm support 22 may be designed so that the elbow is held from 70-110° of flexion.

The arm support 22 can include padding 36 for patient comfort. The padding may be covered by a cloth or fabric structure, which can extend over and around the entire arm support 22. Straps 38 can be provided for maintaining the upper arm and forearm of the patient within the arm support 22. As an example, as shown in the drawing, two large straps 38 may be provided, with one around the upper arm and the other on the lower arm, with a third, smaller strap near the wrist of the patient. The straps 38 press and hold the arm of the patient into contact with the arm support 22 and limit or prevent movement of the arm to aid in immobilization of the shoulder. These straps may be configured to be fully removable, for example by hook and loop fastener, or one end of the strap may be permanently attached to the arm support, with the other removably attached.

The size of the bolster 24 is selected to allow the arm to be held in abduction with respect to the body of the patient P. As an example, the bolster 24 may be of sufficient thickness to maintain the shoulder from greater than 0 to up to 30 degrees of abduction, more preferably from 5-25 degrees of abduction, and still more preferably 10-15 degrees of abduction, with a preferred 10 degrees of abduction.

Figure 3:
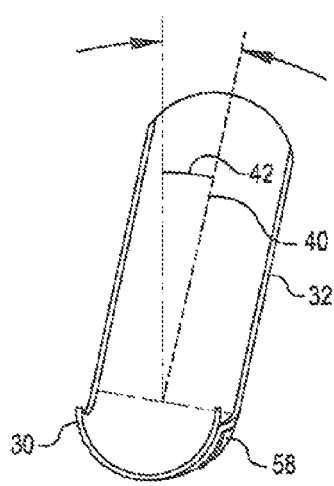
FIG. 3 is a front view of the arm support of FIG. 2, with features removed to show detail of construction for use with a right arm.
Figure 4:
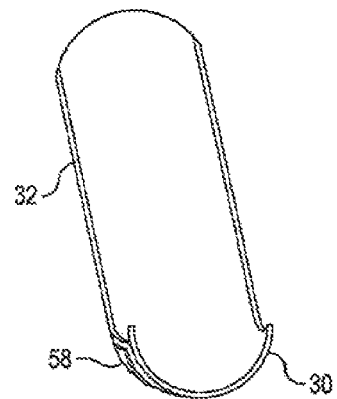
FIG. 4 is a front view of an arm support, similar to FIG. 3, but for a left arm.

The arm support 22 may also be designed to support the arm of the patient P in this functional position with respect to the body. For example, as shown in FIGS. 3 and 4, the upper arm portion 32 may be tilted toward the body of the patient P relative to the lower forearm portion 30 such that when the lower forearm portion 30 is supporting the patient's forearm in a substantially horizontal manner extending mostly outward from the patient's body, the upper arm portion 32 extends at an angle 42 with respect to the horizontal towards the body. Thus, an axis 40 of the upper arm portion 32 extends inward along a line that is consistent with the direction of the upper arm of a patient when the forearm of the patient is spaced apart from the patient's body by the bolster 24. Said in another way, assuming the arm support provides 90 degrees of flexion, if X, Y, and Z axes are defined, with the X and Y axes being in a horizontal plane and the lower forearm portion 30 extending along the X axis and supporting the forearm of the user along the X-Y plane, then the upper arm portion 32 extends at an angle with respect to the Z axis, tilted toward the Y axis, about the X axis. The upper arm portion is perpendicular to the X axis. By providing this arrangement, if a structure is used such as is shown in FIGS. 3 and 4, left and right arm supports 22 are tilted in opposite directions.

Figure 6:
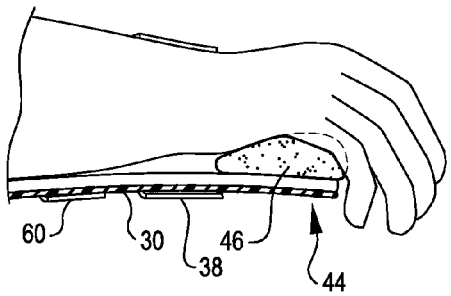
FIG. 6 is a partial sectional side view of the shoulder immobilizer of FIG. 5, but showing an optional wrist pad installed.

In accordance with an embodiment, the lower forearm portion 30 is of sufficient length so that a wrist support area 44 (FIG. 2) fully supports the palm of a patient, and therefore the wrist of the patient, during use. In embodiments, the wrist support area 44 may be ramped upward or otherwise contoured so as to provide extension of the wrist of the patient. For example, wrist extension may be provided from 5-20 degrees. Moreover, in embodiments, an optional wrist pad 46 (FIG. 6) may be provided for removably providing extension of a patient's wrist. Such an option may be advantageous, for example, when the patient is wearing the shoulder immobilizer 20 during typing or use of a computer mouse.

Figure 1A:
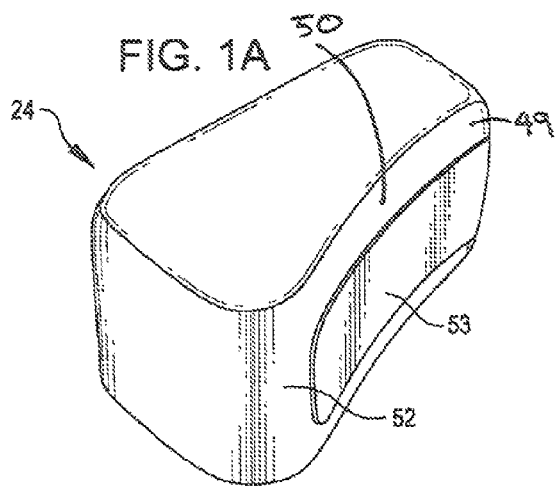
FIG. 1A is perspective view of a bolster for the shoulder immobilizer of FIG. 1.
Figure 2:
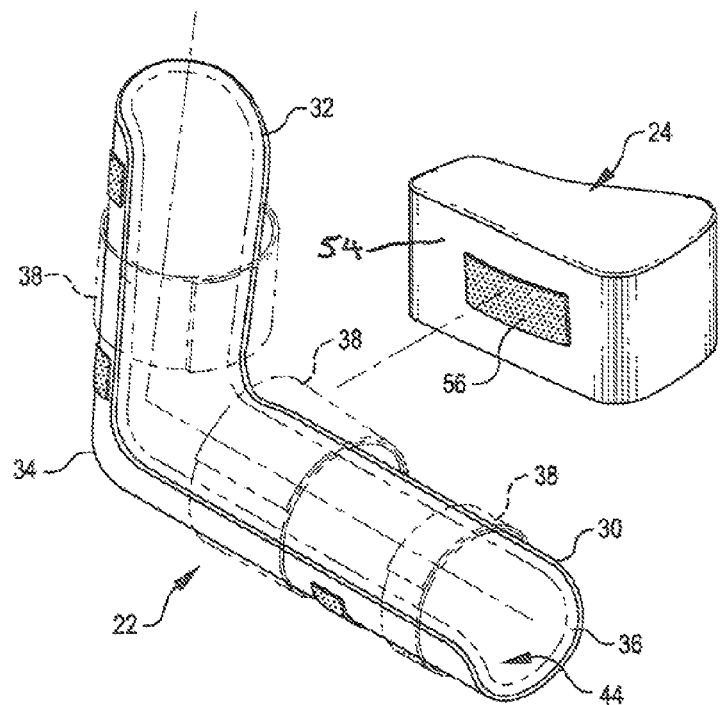
FIG. 2 is an exploded perspective view of an arm support and bolster for the shoulder immobilizer of FIG. 1.

As can be seen in FIGS. 1, 1A and 2, the bolster 24 in the embodiment shown in the drawings is kidney-shaped, but the bolster may take any other shape or form. The bolster 24 may be formed of a suitable material, for example foam or another material that provides comfort for the patient P, and maintains shape for the features described below. The bolster may be, for example, compressible and/or deformable to provide a cushioning function. In the embodiment shown in the drawings, the bolster 24 includes a posterior lobe 49, a concave side 50 that extends against a side of the patient P, and an anterior lobe 52. When installed against a patient, the concave side 50 of the bolster 24 fits against the lower rib cage of the patient P, with the anterior lobe 52 extending across a portion of the front or anterior of the patient, and the posterior lobe contacting a posterior portion of the patient. The lobes 49, 52 resist rotation of the patient's forearm inward. While the posterior lobe 49 and the anterior lobe 52 help to resist the internal rotation of the arm support 30 and the patient's arm, they are not required for the bolster to reduce internal rotation tendency over prior art immobilizers. In addition, if desired, the bolster 24 may be covered with a fabric that resists sliding along a patient P. In embodiments, a sticky or tacky material may be added on the inside surface to further resist sliding. As an example, a nonslip patch 53, for example a patch formed of a non-slip surface, such as a tacky or sticky surface, may be attached on the body-contact side of the bolster 24. An example of a nonslip product is Tough-Tek®/Slip-Not® Non Slip Fabric, a 100% polyester fabric that has a PVC based non-slip surface applied to it. In an embodiment, the bolster 24 includes a flat outer portion 54 that extends against the inside of the lower forearm portion 30 of the arm support 22. The flat outer portion 54 may be permanently affixed to the lower forearm portion 30, or may include releasable fasteners, such as hook and loop fasteners. For example, as shown in the drawings, hook and loop fasteners 56, 58 are positioned on the flat outer portion 54 and the lower forearm portion 30 (FIGS. 2 and 3).

In embodiments, the bolster 24 is configured so that, when set against the side of a patient P with the arm support 22 attached to the bolster, the arm of the patient is held in either neutral rotation (i.e., straight outward from the body), or 10-15 degrees of external rotation (i.e., extending slightly outward from the body). The flat outer portion 54 and the attachment of the bolster 24 to the arm support 22 aid in maintaining the arm in this position, and resist internal rotation of the arm (i.e., movement of the hand toward the stomach).

Figure 5:
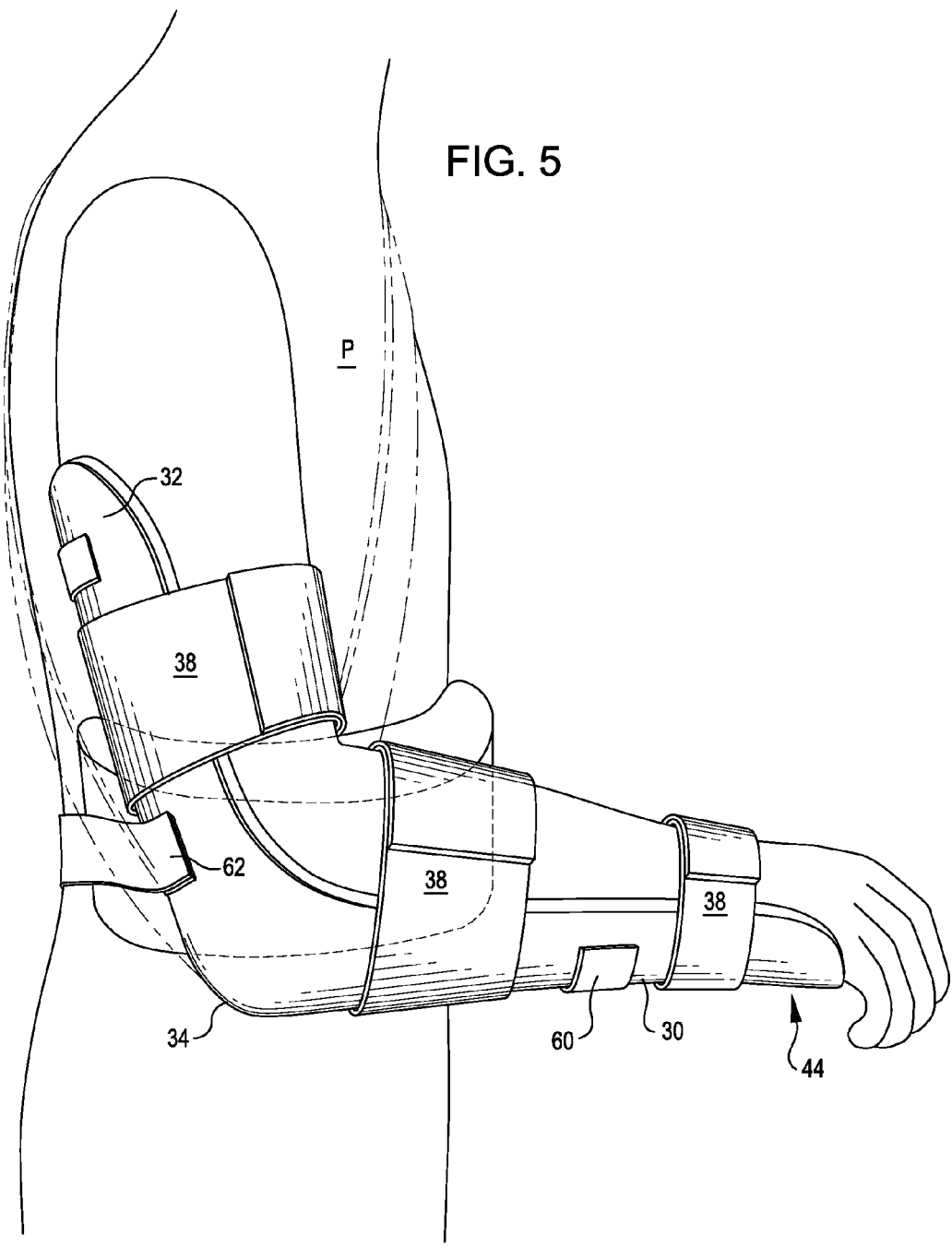
FIG. 5 is a side view of the shoulder immobilizer of FIG. 1.

To lock the arm support 22 into position to the user's body, a body strap 26 holds the arm support 22 in place against the body of the patient. The body strap 26 anchors the arm support 22 to the body and, if the bolster 24 is used, wedges the bolster 24 between the body and the arm support. In embodiments, the body strap 26 may include a front anchor 60 (FIG. 5) for attaching to the full lower forearm portion 30, and a rear anchor 62 for attaching to the upper arm portion 32. Each of these may be releasably attached, such as by hook and loop fasteners, B-rings, buckles or other suitable fasteners. It is also understood that the body strap 26 may have multiple attachment points on either arm support 22. For example, as shown in FIG. 5, the rear anchor 62 is located at the lower end of the upper arm support. There could be an additional rear anchor (not shown) located at the upper end of the upper arm support in order to distribute the forces over the length of the arm support. This additional rear anchor could be could be connected with the body strap 26 via a "y" or "yoke" type configuration.

Thus, the body strap 26 attaches to the lower forearm portion 30, wraps around the trunk or torso of the patient, and attaches at the rear anchor 62 to the upper arm portion 32. In embodiments, the body strap 26 is formed of elastic so that it may pull the arm support 22 and bolster 24 into place against the patient's body with minimal discomfort, but providing tensioned anchoring to the patient. In this manner, the anterior lobe 52 and flat outer portion 54 aid in maintaining the arm in the neutral or exteriorly rotated position.

As an alternative to elastic, the body strap 26 may be any structure which permits the arm support 22 to be pulled, tensioned, or otherwise locked against a patient's body (with the bolster 24 in between, if used). Cinching mechanisms, tighteners, well fitted straps, or other structure and mechanisms may be utilized to ensure that the strap anchors the arm support into place against the patient's body. The anchors of the body strap 26 to at the posterior and anterior of the arm support provide a wide separation between the two points of contact, further ensuring that internal rotation does not occur.

The rigid arm support 22, the bolster 24, and the body strap 26 provide shoulder immobilization for a patient. The arm support 22, because it is made of a rigid or semi-rigid material, maintains the arm in a desired angle of flexion. The bolster 24, utilizing the lobe 52 and the flat outer portion 54, maintains the arm in suitable rotation, such as neutral or external rotation. The body strap 26 holds the bolster 24 and the rigid arm support 22 in place, and ensures this connection. The body strap 26, by pulling and/or maintaining the arm support into contact with the patient P, ensures that the friction provided by the outer surface of the bolster 24 is utilized to resist sliding of the bolster along the patient's body, resisting internal rotation of the arm. Thus, features that prevent internal rotation are the kidney shape of the bolster 24, the anterior lobe 52 and its engagement with the front of the patient's body, the friction provided by the exterior surface of the bolster 24, the engagement of the arm support 22 along the flat outer portion 54 of the bolster, and the elasticity of the body strap 26 which holds the bolster features in place against the patient's body, and the contact of the arm support 22 with the flat outer portion of the bolster. Moreover, the flat outer portion 54 resists the rigid arm support 22 rotation around the bolster 24. Again, this connection is maintained and made more solid by the elastic body strap 26.

An advantage of the shoulder immobilizer 20 is that the device provides both full immobilization and comfort both for daytime and nighttime use. Conventional immobilization strategies involve use of either a soft sling, which provides only partial immobilization, or a gunslinger type of immobilizer, which is rigidly attached to the patient's body and thus is uncomfortable for daily and nighttime use due to the absolute rigidity of the brace. In contrast, the shoulder immobilizer provides both comfort and support. The rigid or semi-rigid arm support 22 provides greater security and support than a sling. The body strap 26 comfortably anchors the arm support 22 to the patient's body without need for a rigid structure connected to the patient's body. If used, the bolster 24 may provide cushioning of the arm support against the patient, and permits the arm support to be securely placed against the patient's body, via the body strap 26, without discomfort.

Embodiments may utilize the arm support 22 and the body strap 26 without use of the bolster 24. Anchoring of the body strap 26 directly to the arm support 22 permits the body strap 26 to be used as the sole strap or other feature for immobilization. By anchoring the body strap 26 at the anterior and posterior of the patient's body, the user's arm is placed automatically into neutral or even external rotation. The body strap 26 pulls or tensions the arm support into this position, maintaining immobilization without a shoulder strap, and if desired, without the bolster 24.

For some situations, however, there may be a need for more abduction, for example in a repair of massive rotator cuff tear. As such, an abduction bolster, such as the abduction bolster 24, may be used to provide sufficient abduction positioning.

Due to the solid connection made by the rigid arm support 22, the bolster 24 and the body strap 26, a shoulder or neck strap is not required for shoulder immobilization or for partial arm support. However, in alternate embodiments, a shoulder strap (e.g., the shoulder strap 28) may additionally be provided to add additional support for the shoulder immobilizer 20.

An advantage of the shoulder immobilizer over prior art fabric pouches is that a substantial portion of the patient's arm is exposed, permitting access to the arm, for cold therapy, as an example. In the case of cold therapy, tubing may be routed to and around the arm without the pouch being in the way.

Figure 15:
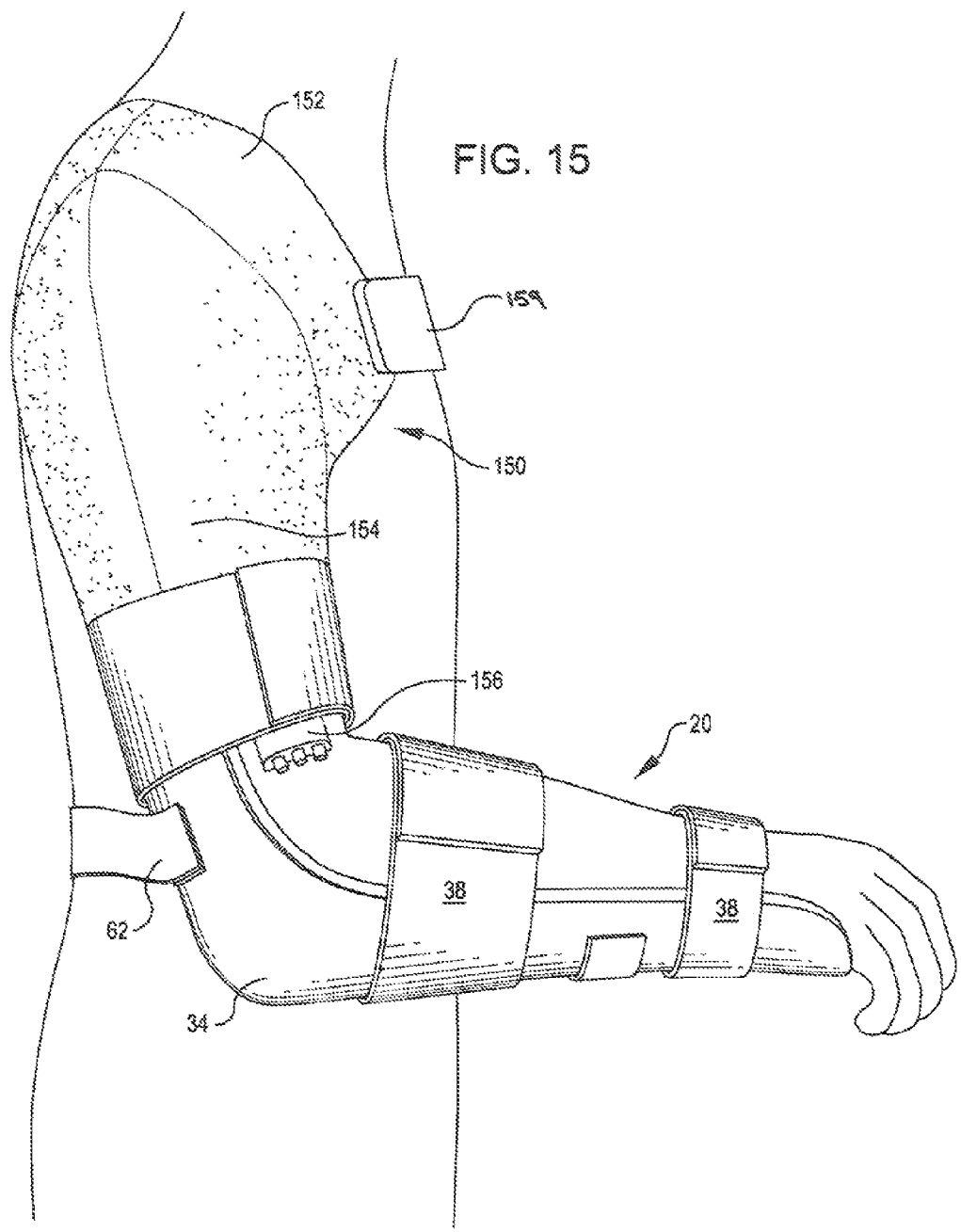
FIG. 15 shows a side view of an embodiment of a shoulder immobilizer used in connection with a cold therapy unit in accordance with embodiments.

Cold therapy is commonly used in conjunction with immobilization following shoulder surgery. Several companies make units for cold therapy which include a fabric pad that is wrapped around the shoulder. Current marketed cold therapy systems include Game Ready® Cold Therapy System, Breg®-Polar Care® Cold Therapy System, DJO®-Iceman Cold Therapy System, Ossur®-Cold Rush® Cold Therapy System, DeRoyal®-Cold Therapy System, and EBI®-EBice® Cold Therapy System. A separate cooler box pumps cold water into the pad via a flexible tubing. As an example, FIG. 15 shows a side view of an embodiment of the shoulder immobilizer 20 used in connection with a cold therapy pad 150. The cold therapy pad 150 includes a shoulder region 152 that extends over the top of and around the front and back side of the shoulder. An arm portion 154 extends down the arm of the user and into the rigid or semi-rigid arm support 30. A plug 156 may be included for connecting to the cooler box/pump (not shown) via flexible tubing (also not shown).

The fact that the shoulder immobilizer 20 is open at a front side at the upper arm region, and a top side of the forearm region, permits easy connection of the cold therapy device 150 and routing of flexible tubing and the plug 156 in the shoulder immobilizer. A separate chest strap 159 extends around the chest of the user to hold the cold therapy device 150 in place.

In an alternate embodiment, as shown in FIGS. 16 and 17, a butterfly style cold therapy unit 160 may be utilized with a shoulder immobilizer 20.

For the butterfly style cold therapy device 160, two tabs 162, 164 may be provided toward the bottom, arm portion of the device. Each of these tabs 162, 164 may include an attachment structure, such as a hook or loop fastener 166, 168 for attaching or integrating with the shoulder immobilizer 20. In an embodiment, the fasteners 166, 168 are attached directly to the arm support 34 for the shoulder immobilizer 20. In an alternate embodiment, a strap 170 may be provided having fasteners 172, 174 that are attached to the fasteners 166, 168. As shown in FIGS. 16 and 17, the strap 170 extends around the back side of the arm support 34. In an alternative embodiment, the strap 170 may be integral with the cold therapy device 160.

Although the tabs 166, 168 are shown as being routed on the outside of the arm support 30, the tabs 166, 168 may extend into and/or attached to the inside of the arm support. By allowing direct attachment to the arm support 34, the butterfly style cold therapy device 160 may be advantageously placed and maintained in position on a user and used with the shoulder immobilizer 20.

Figure 7:
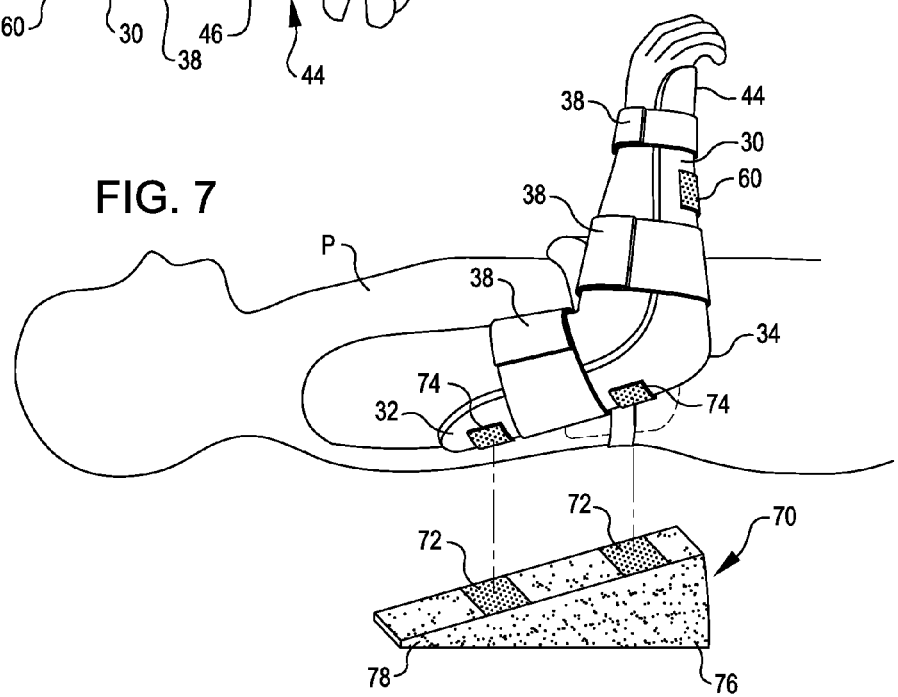
FIG. 7 is an exploded view showing a back sleeping pad before attachment to parts of the shoulder immobilizer.
Figure 8:
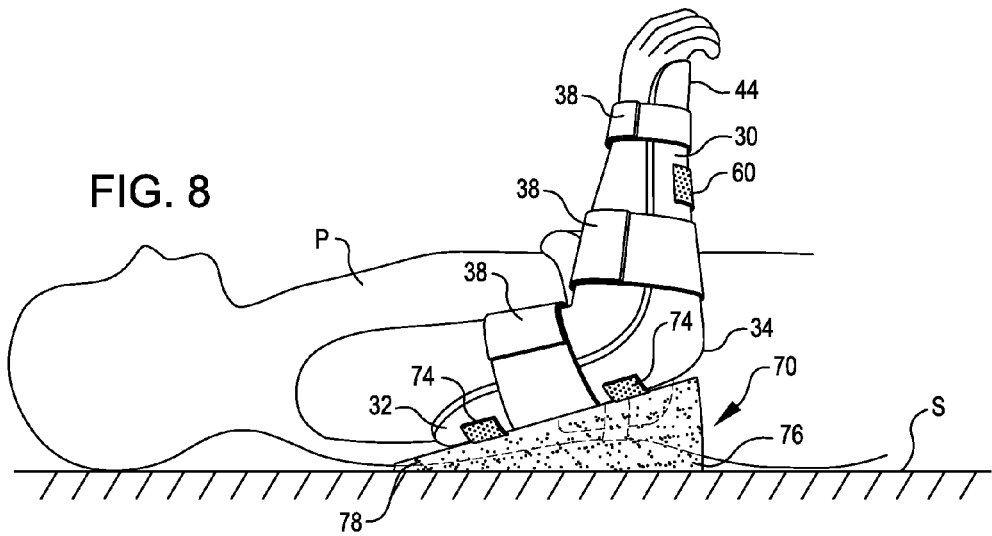
FIG. 8 is a side view of the shoulder immobilizer and back sleeping pad of FIG. 7, shown installed on a patient.

In accordance with additional embodiments, as shown in FIGS. 7 and 8, a base 70 (in the form of a back sleeping pad) may be provided that is removably attached or permanently attached to the upper arm portion 32 of the arm support 22. The base 70, because of its posterior positioning, engages a surface S, such as a bed, and spaces the patient's elbow from the surface.

If desired, the base 70 may include releasable fasteners, such as hook and loop fasteners 72, 74 for attaching the back sleeping pad 70 to the upper arm portion 32.

To provide spacing of the patient's elbow from the surface S, the back sleeping pad 70 may taper in thickness downward from the elbow region 76 to a shoulder region 78. In this manner, the shoulder is not uncomfortably moved away from the surface S, but the elbow is conveniently supported at an upward position. A bottom surface of the back sleeping pad 70 may be flat to resist rotation of the back sleeping pad 70 and the patient's arm. The back sleeping pad 70 also helps to maintain the shoulder in a neutral position by preventing the shoulder from pivoting or rotating forward or backward. The top surface of the back sleeping pad 70 may be flat or contoured to receive the arm support 34.

The rigid or semi-rigid arm support 22 and the posterior back sleeping pad 70 resist the shoulder from moving forward because the elbow, by being at approximately equal height or higher than the shoulder, prevents a rotation of the shoulder upward when lying down. In many prior art shoulder braces, there is a tendency for the arm to slip backward and the shoulder to move forward (upward when lying down), which reduces stability of the shoulder. Raising of the elbow by the back sleeping pad 70 resists this tendency.

Thus, the combination of the back sleeping pad 70 and the rigid or semi-rigid arm support 22 provides shoulder stability, specifically preventing shoulder extension, while the patient P is lying down. Alternate embodiments may be provided, and in general provide a stable base to prevent rotation and spacing of the elbow from the surface S.

Figure 9:
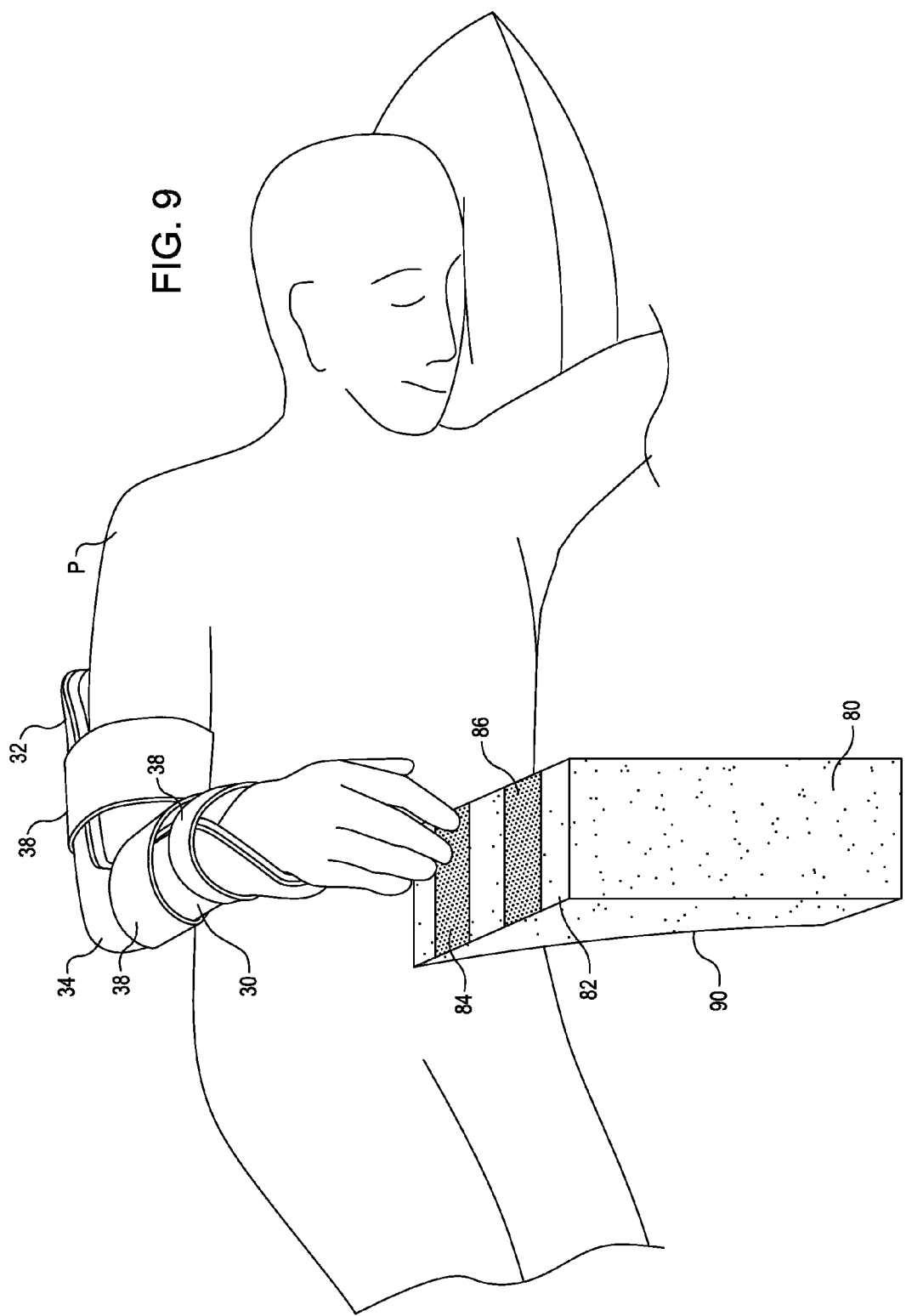
FIG. 9 is an exploded view showing a side sleeping pad before attachment to parts of the shoulder immobilizer.
Figure 10:
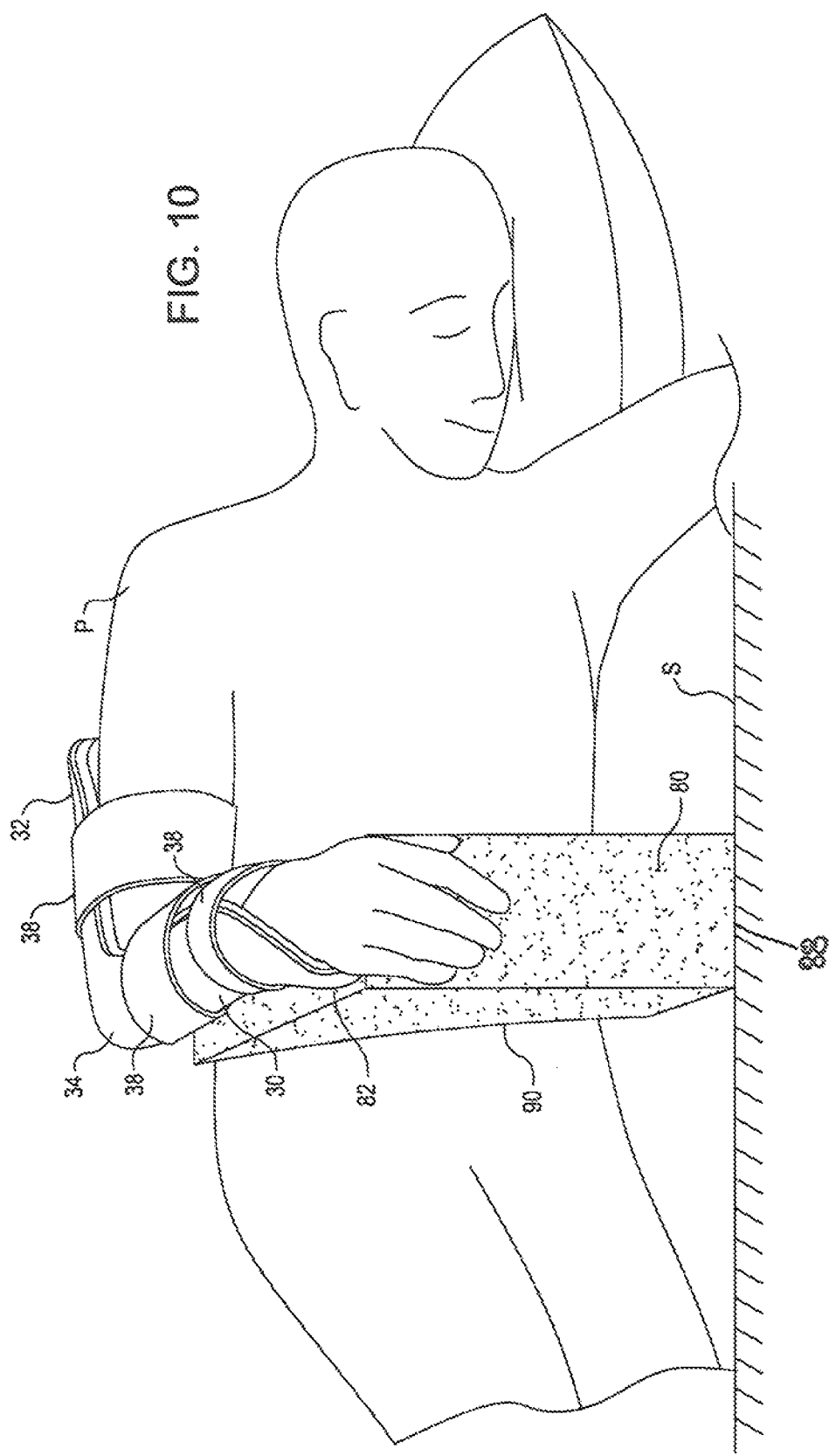
FIG. 10 is a side view of the shoulder immobilizer and side sleeping pad of FIG. 9, shown installed on a patient.

In accordance with another embodiment, a side sleeping base, in the form of a side sleeping pad 80 (FIGS. 9 and 10) is provided for permitting the patient P to lie on his/her side and have the patient's shoulder supported during sleep. To this end, the side sleeping pad 80 extends between the arm support 22 and a surface S, such as a bed, while the patient is lying on the bed. The side sleeping pad 80 includes a top 82 that may be connected, for example, by releasable fasteners to the arm support 22. These releasable fasteners may be, for example, hook and loop fasteners 84, 86 (FIG. 9). One end of the wrist strap 38 may be released from the lower arm support 30 and attached to the side sleeping pad 80 to provide additional security. The top 82 may be flat or may be otherwise contoured to receive the arm support 22.

A bottom 88 of the side sleeping pad 80 may be, for example, flat so as to stabilize against the surface S. In an embodiment, a posterior side of the side sleeping pad 80 includes a concave surface 90 for fitting against the patient. This concave surface 90 may be, for example, arranged so that the top 82 of the side sleeping pad 80 is wider than the bottom 88 of the side sleeping pad, allowing the top to extend further along the patient's arm, and thus support the patient's arm, preventing internal rotation of the arm when the patient is lying on a side.

The back sleeping pad 70 and the side sleeping pad 80 provide two different structures for allowing a patient to lie on his/her back or side and yet still have the shoulder of the patient immobilized with the arm support 22. Many prior art shoulder immobilization devices have required that a patient sleep in a chair or risk unstable positions of the shoulder. Thus, the back sleeping pad 70 and the side sleeping pad 80 provide a much needed feature for shoulder immobilization. Moreover, the back sleeping pad 70 and/or side sleeping pad 80 may be used with any arm support such as a sling; not necessarily a rigid or semi-rigid arm support. The back sleeping pad 70 and the side sleeping pad 80 are embodiments of support bases that interface with the arm supports to provide proper positioning and immobilization of the shoulder while a patient is lying down. Other embodiments may include bases that are inflatable or adjustable in height and/or width. One such method of adjustability could include the stacking of smaller bases to achieve a desired height for a given patient.

Figure 11:
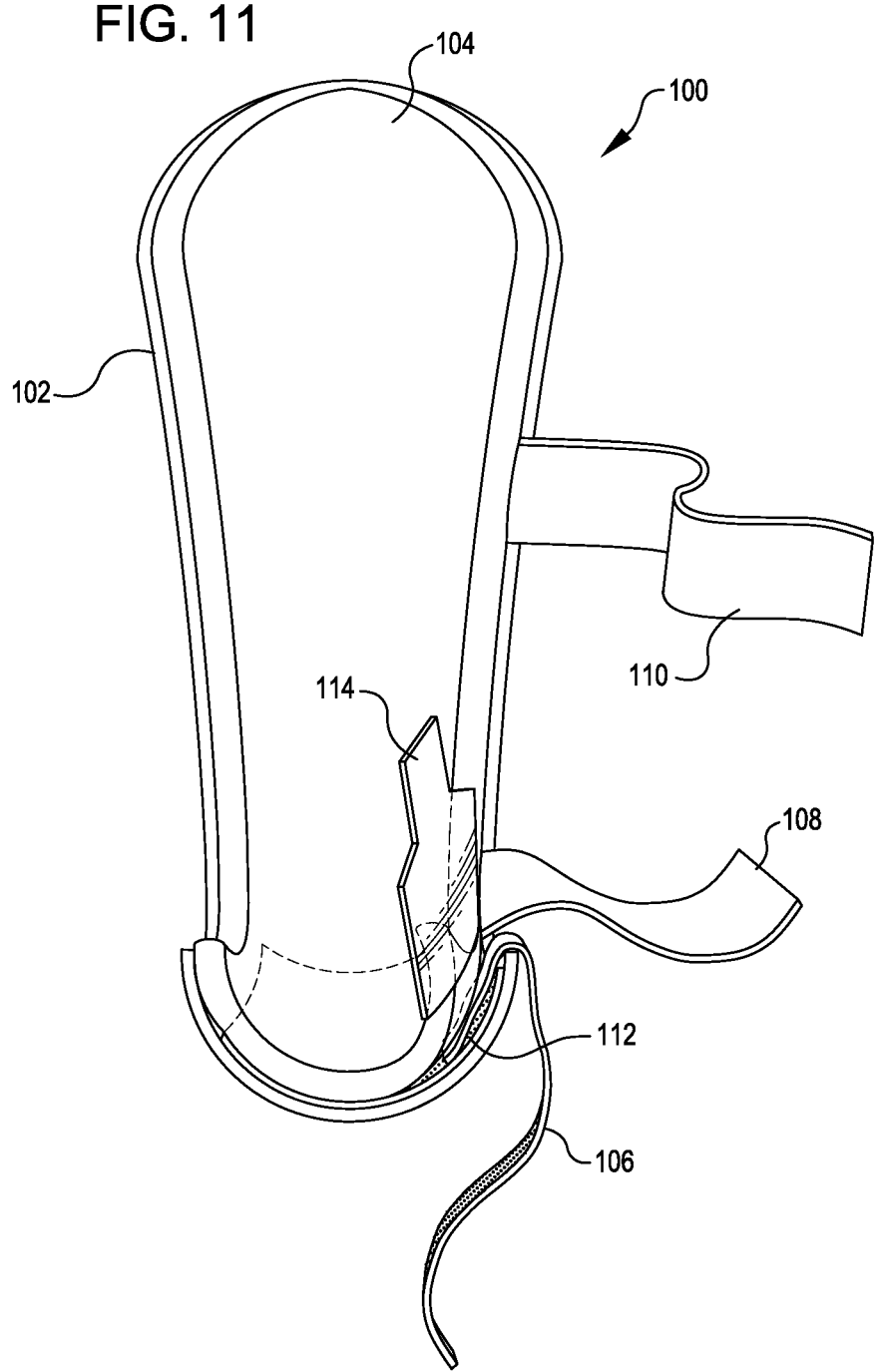
FIG. 11 is front view of an alternate arm support in accordance with embodiments.

FIG. 11 shows an alternate arm support 100 in accordance with embodiments. The arm support 100 is interchangeable, in that it may be used for either the left or right arms, instead of being made to fit only a left arm or a right arm.

The arm support 100 includes a rigid or semi-rigid core 102, with padding 104 fitted in the areas of the core that contact the arm of the patient and/or extending around desired portions of the core. A fabric covering (not shown) may extend over and/or around the arm support, and may be separate from or integrated with the padding 104.

The arm support 100 includes a number straps to hold a patient's arm in place. In the embodiment shown in the drawings, there are three straps 106, 108, 110, but another number may be used. In accordance with embodiments, these straps 106, 108, 110 are interchangeable to opposite sides of the arm support 100 dependent upon whether the arm support is to be used with a left arm or right arm. To this end, the straps are releasably connectable to a side, for example by hook and loop fasteners.

In an embodiment, hook or loop fasteners 112 (only one shown in the drawing) are provided between the padding 104 and the core 102, on the core. The end of a strap (e.g., the strap 106) is inserted between the padding 104 and the core 102, and is connected to the fastener 112. The end of the strap includes a hook and loop fastener (not shown) for this purpose.

In the event where a fabric covering (not shown) extends over and around the arm support 100, slots may be provided to insert the straps between the padding and core. To insert a strap in a slot, a tool 114 may be provided. This tool 114 is sufficiently wide to cover the strap 106 when the strap in inserted into the slot. To insert the strap, the tool is aligned against the strap, with the hook and loop fastener on the strap against the tool, and the tool and strap are inserted into the slot. The tool 114 blocks connection of the two hook and loop fasteners (112 and the fastener on the strap), permitting insertion. The tool 114 may then be removed from the strap by pulling outward, leaving the strap in place. The two fasteners may then be connected, for example by pressing downward on the padding 104 to make the connection. The tool 114 may be used in a similar manner to attach the straps to the outside surface of the core 102.

Figure 12:
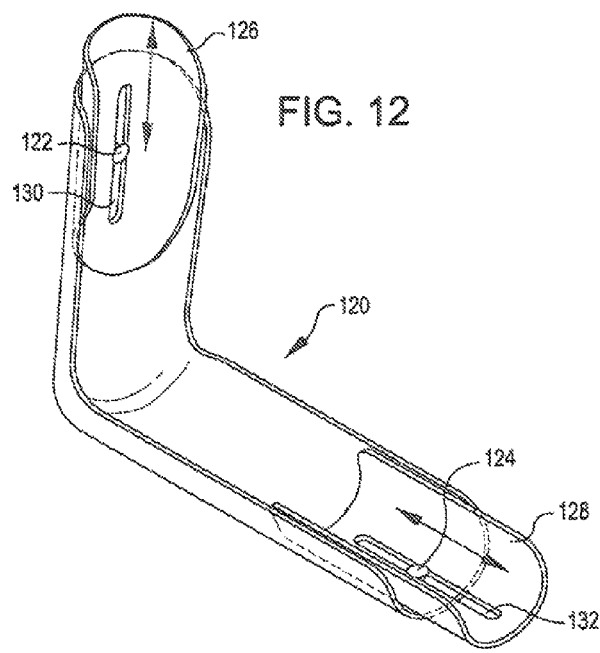
FIG. 12 shows a rigid or semi-rigid arm support having support length adjustability in accordance with embodiments.

FIG. 12 shows a rigid or semi-rigid arm support 120 having support length adjustability in accordance with embodiments. In accordance with the embodiment shown in FIG. 12, the forearm and upper arm region of the rigid or semi-rigid arm support 120 are adjustable in length to support various different size arms and/or to support different sections of a patient's arm, such as permitting support of a patient's wrist or not. In embodiments shown in the drawings, the extension portion of the upper arm portion and the wrist portion are both adjustable, but only one of these may be adjustable in alternate embodiments.

In the embodiment shown in the drawings, the rigid or semi-rigid arm support 120 includes fasteners 122, 124 extending out of the upper arm portion and wrist portion, respectively, of the rigid or semi-rigid arm support 120. An upper sliding plate 126 is mounted for movement within the upper arm portion of the rigid or semi-rigid arm support 120. This upper arm slide plate 126 may slide along a track, may be conformed to slide along the upper arm portion of the rigid or semi-rigid arm support 120, or may otherwise be structured so that it may move along the support. A similar lower arm sliding plate 128 is mounted adjacent a wrist portion of the rigid or semi-rigid arm support 120. The upper and lower sliding plates 126, 128 include slots 130, 132 that fit on the fasteners 122, 124. The engagement of the fasteners 122, 124 in the slots 130, 132 permits sliding movement of the upper and lower sliding plates 126, 128 to adjust the overall length of the upper arm portion and lower arm portion, respectively, of the rigid or semi-rigid arm support 120.

The fasteners 122, 124 may be friction fit into the slots 130, 132 so as to provide resistance to movement of the upper and lower sliding plates 126, 128. Alternatively, the fasteners may include wing nuts, tool receiving heads, or other structures that allow tightening and loosening of the fasteners so as to alternatively allow release and sliding of the upper and/or lower sliding plates 126, 128, or lock the plates into place.

The sliding movement of the sliding plates 126, 128 permits the rigid or semi-rigid arm support 120 to be sized to a particular user. To this end, the sliding plates 126, 128 may be formed of a rigid or semi-rigid material and provide similar support to a patient as the remainder of the arm support 120. The adjustable arm support in FIG. 12 thus provides variability for a variety of patient sizes and/or uses. Other structures may be provided for varying the support and/or size provided by the rigid or semi-rigid arm support, including folded-out extensions, inflatable extensions, and so forth.

Figure 13:
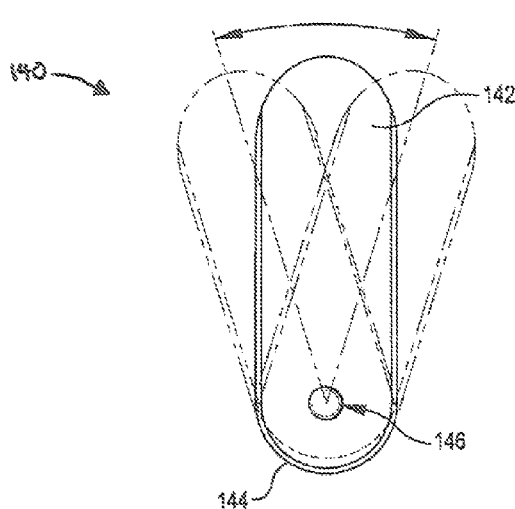
FIGS. 13 and 14 show an end view and side view, respectively, of a rigid or semi-rigid arm support that pivots to provide a desired abduction angle in accordance with embodiments.
Figure 14:
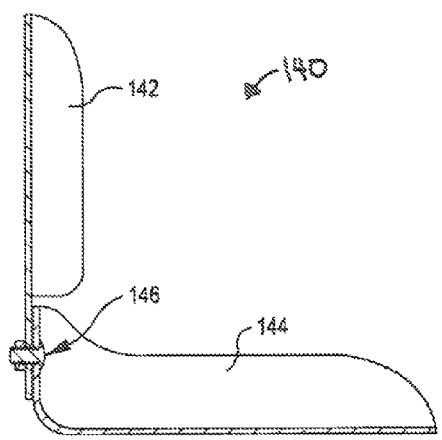

FIGS. 13 and 14 show an end view and side section view, respectively, of a rigid or semi-rigid arm support 140 that pivots to provide a desired abduction angle in accordance with embodiments. The rigid or semi-rigid arm support 140 includes an upper arm portion 142 attached to a lower arm portion 144 at a pivot 146. In the embodiments shown in the drawings, the pivot is a fastener, but other pivot structures may be provided. As an example of a fastener, a nut and bolt may be used as a pivot.

In embodiments, the pivot 146 may be loosened or otherwise may release the lower arm portion 144 and upper arm portion 142 for pivoting movement so that the upper arm portion 142 may rotate relative to the lower arm portion 144 as shown by the arrows in FIG. 13. This pivoting motion allows the upper arm portion 142 to move to the left or right relative to the lower arm portion 144. In this manner, a single, rigid or semi-rigid arm support 140 may be utilized for either the left or right arm of a user. In addition, the abduction angle for a user may be adjusted for a desired support angle and/or bolster.

Although a single pivot is shown in the drawings, an arm support may include more than one pivot or a different pivoting structure. In addition, although the fastener pivot 146 is loosened to allow pivoting, a friction attachment or other arrangement may be provided at the juncture of the upper and lower portion.

Figure 32:
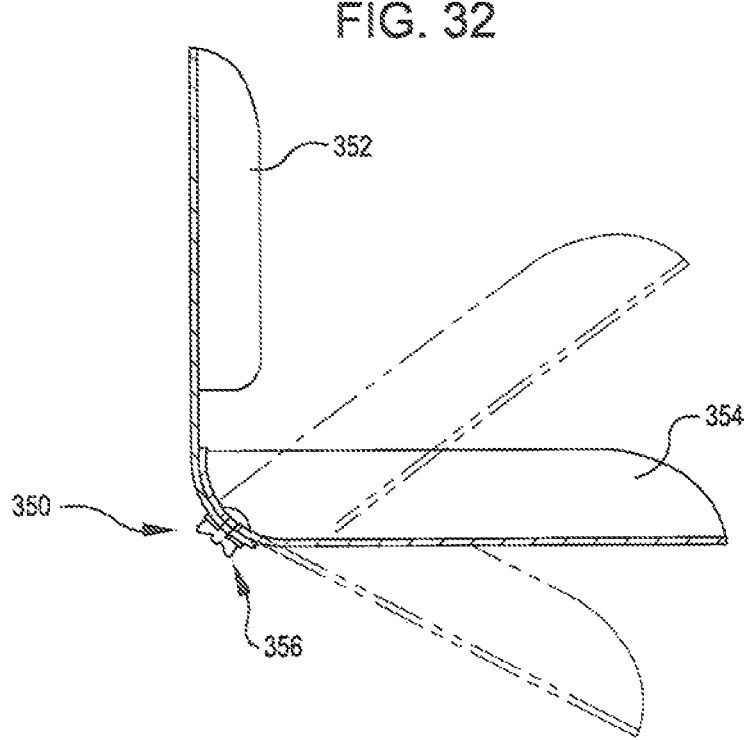
FIGS. 32 and 33 show an arm support that is adjustable at an elbow angle in accordance with embodiments.
Figure 33:
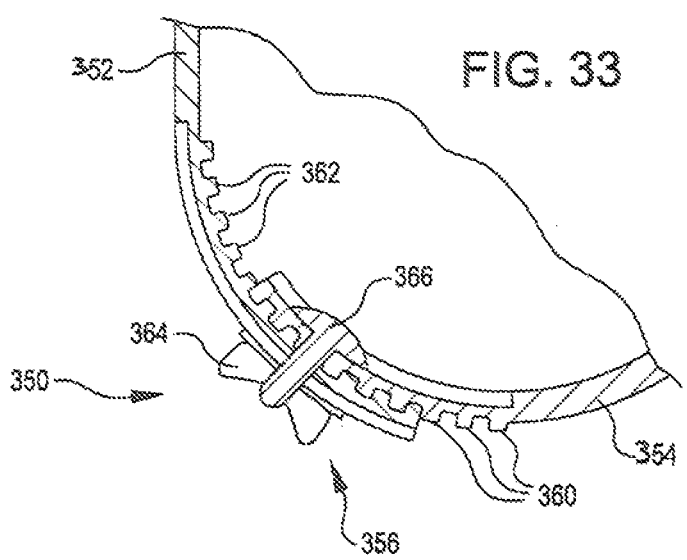

In accordance with another embodiment, as shown in FIGS. 32 and 33, an arm support 350 may be hinged so as to alter the angle of a patient's elbow that is supported arm support. To this end, the arm support 350 may include a hinge, a pivot, or any other structure that allows adjustment of the elbow and then locking of the arm support at the desired angle.

As one example, the arm support 350 includes an upper arm support section 352 and a lower arm support section 354 connected at an adjustment mechanism 356. In the embodiment shown in the drawings, the adjustment mechanism 356 includes serrations 360, 362 on mating, arched surfaces of the upper and lower arm supports 352, 354. A wing nut 364 and bolt 366 hold the two sets of serrations together, and lock the upper arm support section 352 and the lower arm support section 354 into position. The wing nut 364 may be loosened to permit the two support sections 352, 354 and to align different sets of serrations so that a different angle may be formed.

FIG. 18 shows a bolster that may be adjustable in width so as to vary the abduction angle of an immobilized arm in accordance with embodiments. In general, the expandable bolster 190 is capable of expanding or contracting to a desired size so to set a desired abduction angle of the patient's supported arm. In embodiments, the bolster 190 includes sidewalls 192, 194, each of which may include a frame with cushioned outer surfaces 196, 197. An expandable section 198 is positioned between the two frames with cushioned outer surfaces 196, 197. The expandable section 198 allows the two frames with cushioned outer surfaces 196, 197 to be moved toward and apart from one another. Moreover, using the expandable section 198, with the fixed shape sidewalls, permits the two frames with cushioned outer surfaces 196, 197 to maintain their shape during expansion. Instead of deforming the outer ends, the distance between the two frames with cushioned outer surfaces 196, 197 changes as the expandable section is expanded or contracted. If desired, a fabric, such as elastic, may be provided over the expandable section 198.

In embodiments, expansion of the expandable section 198 may be provided by a variety of different mechanisms, including an inflatable bladder, a worm gear, or any other suitable pneumatic, hydraulic, mechanical, or other expandable or movable structure. In one such embodiment, multiple thinner center sections (equivalent to expandable section 198), could be stacked to provide a desired width. These thinner sections would be inserted and withdrawn to achieve a desired width.

In an embodiment shown in FIGS. 19, 20, and 21, the expandable section 198 includes concave inner surfaces 200, 202 on the inside of the frame with cushioned outer surfaces 196, 197. Each of the concave inner surfaces 200, 202 includes serrations 204, 206. A centrally-mounted rod 208 having stops 210 at distal ends is connected to a control knob 212 (FIGS. 18 and 19) positioned on the outside of the expandable bolster 190. The control knob 212 and the rod 208 are fixed for rotation together.

To expand or properly size the expandable bolster 190, the control knob 212 is rotated, causing the stops 210 on the ends of the rods 208 to step along and engage within opposite sets of the serrations 204, 206. At each pair of opposing serrations, the sidewalls 192, 194 are spaced a defined distance apart from one another. The desired spacing of the sidewalls may be chosen by rotating the control knob 212 clockwise or counterclockwise as needed.

The expandable properties of the bolster 190 may be utilized for the back and side sleeping pads described above so as to provide adjustable sleeping pads that may fit a particular patient. As an example, a side sleeping pad, shaped like a side sleeping pad 80, may have an expandable middle section so that it may adjust for various torso widths of patients.

Figure 22:
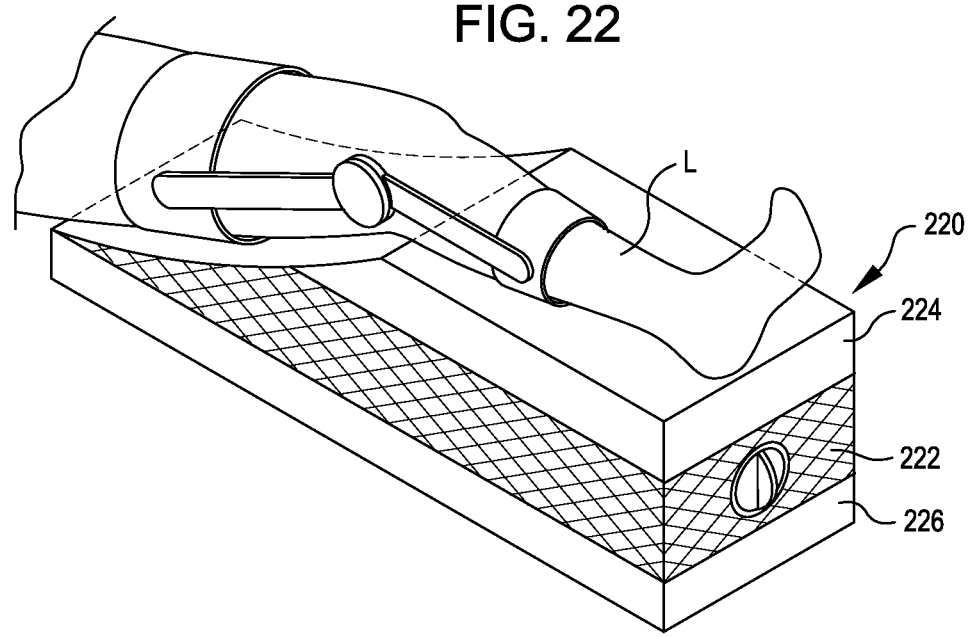
FIG. 22 shows an expandable bolsters for supporting a leg of a patient.

Expandable bolsters may be used for supporting the patient in other positions, such as to support the leg L of a patient, as shown in FIG. 22. For the bolster 220 shown in FIG. 22, the expandable section 222 is arranged between a top section 224 that is engageable by a leg L of a user and a bottom section 226. The bottom section 226 is placed against the bed of the user. The bolster 220 may be adjusted according to leg length and/or a desired height for the user's lower leg.

Fracture Stabilization Device

In accordance with embodiments, the arm support 30 may be used with a fracture stabilization or compression plate so as to stabilize a fracture during a healing process. Although described as a "plate," the compression plate may be any structure which engages the portion of the arm not fully contacted by the arm support 30. To this end, the arm support 30 provides one portion of a compression fitting around the user's fracture, with the compression plate completing at least a substantial, if not full, encapsulation of the fracture.

An advantage to using the arm support 30 as a portion of a fracture stabilizer/compression device is that the arm support allows the patient's arm to hang, thus lending support to the arm while keeping the bone aligned via tension. Thus, the combined use of the arm support 30 with the fracture brace allows distraction and alignment from the hanging arm support 30, plus compression from the fracture compression plate. A bolster may or may not be used with the combined compression plate and arm support 30. In addition, the waist body strap 26 may or may not be used with this combination, but very often will be used to prevent excessive rotation of the arm. Unlike prior devices, a sock is not needed for capturing the pressure plate and holding it in position. These socks are uncomfortable to take on and off. In addition, the compression plate can easily accommodate swelling, since it is adjustable. When the braces are used in conjunction with the sleeping bolsters, the hand can be elevated. This reduces swelling of the hand and upper extremity, reducing the risk of compartment syndrome, a feared complication of forearm fractures. Moreover, the removable compression plate allows easier monitoring of compartment pressures than traditional casts or splints.

As described below, fracture braces may be used in compression of various areas of the upper extremities, including shoulder, humeral shaft, distal humeral, elbow, full arm, and wrist fractures. The compression devices usually will apply and save time for staff because plaster and/or fiberglass are not needed, so there is no cleanup time. The device is radiolucent because embodiments use no metal. Patient care is simplified, particularly for scaphoid fractures, because there is no need for long arm thumb spica cast.

Figure 23:
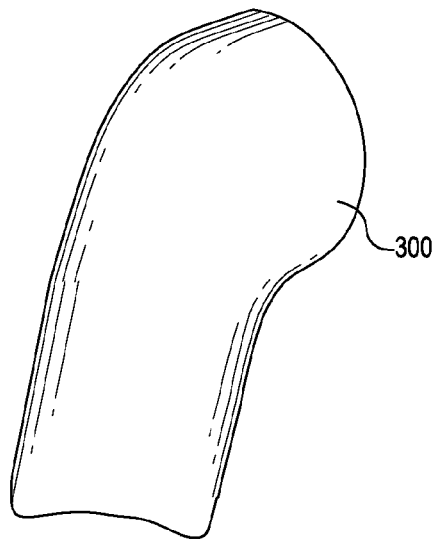
FIGS. 23 and 24 show a shoulder compression plate designed to fit over and around an outer portion of the shoulder and down a portion of the upper arm of the user.
Figure 24:
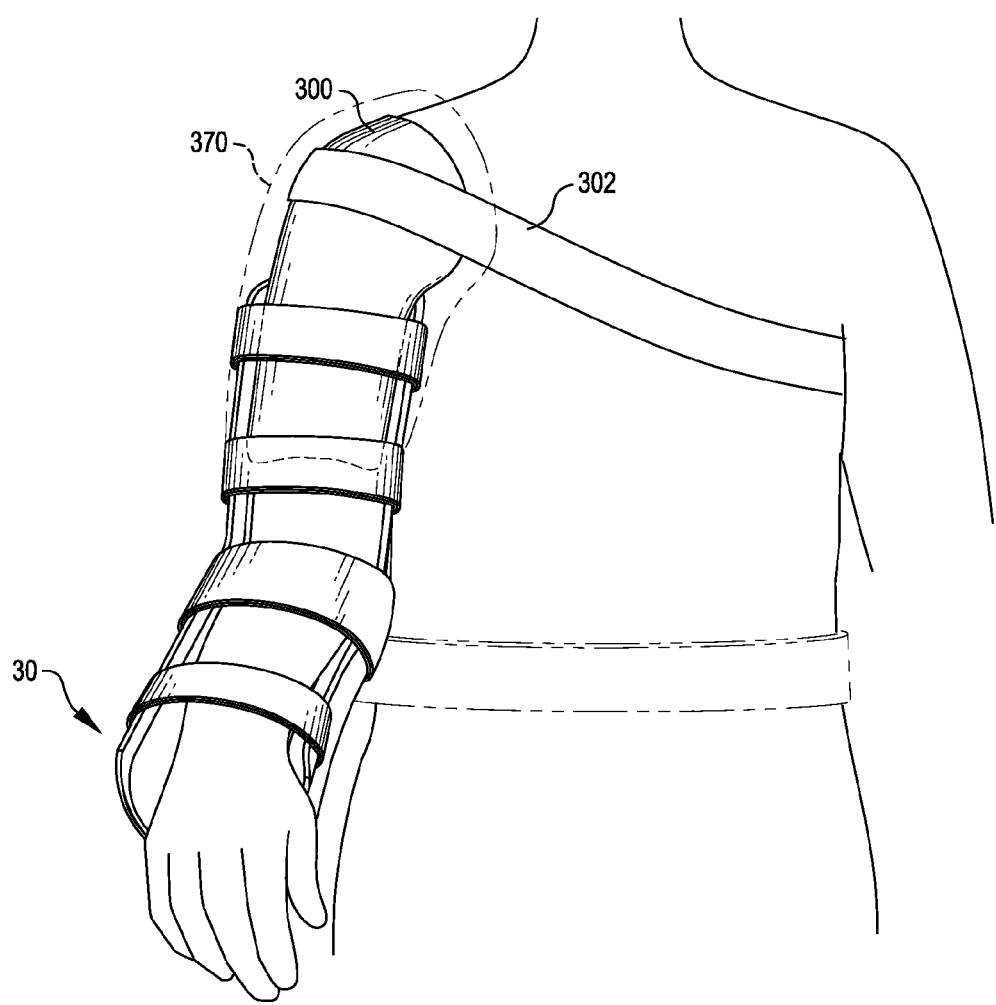

A first embodiment of a compression plate is shown in FIGS. 23 and 24, where a shoulder compression plate 300 is designed to fit over and around an outer portion of the shoulder and down a portion of the upper arm of the user. Such a shoulder compression plate 300 will often be used in combination with an upper shoulder strap 302 to maintain the shoulder compression plate 300 in position. Such a shoulder compression plate 300 can be utilized for a humeral shaft fracture, particularly proximal fractures. The advantage to using such an over-the-shoulder compression plate is that it provides compression around the fracture. This compression plate is particularly advantageous when used in combination with the arm support 30, because the arm support aligns the bone using tension (gravity). The waist/body strap prevents unwanted rotation.

If desired, a cold therapy device, as described above, may be attached to the outer surface of the compression plate 300, for example by hook and loop fasteners. This feature provides an integrated cold therapy, stabilization, and compression device. For example, as shown in FIG. 24, a cold therapy device 370 may fit over, and be attached to, the compression plate 300.

Figure 25:
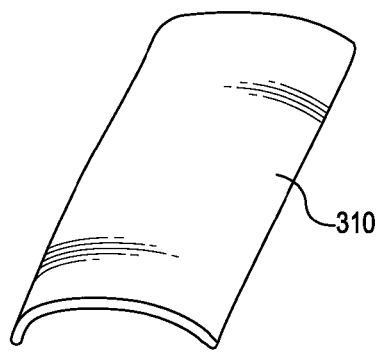
FIGS. 25 and 26 illustrate another embodiment of a compression plate for use on a forearm of a user.
Figure 26:
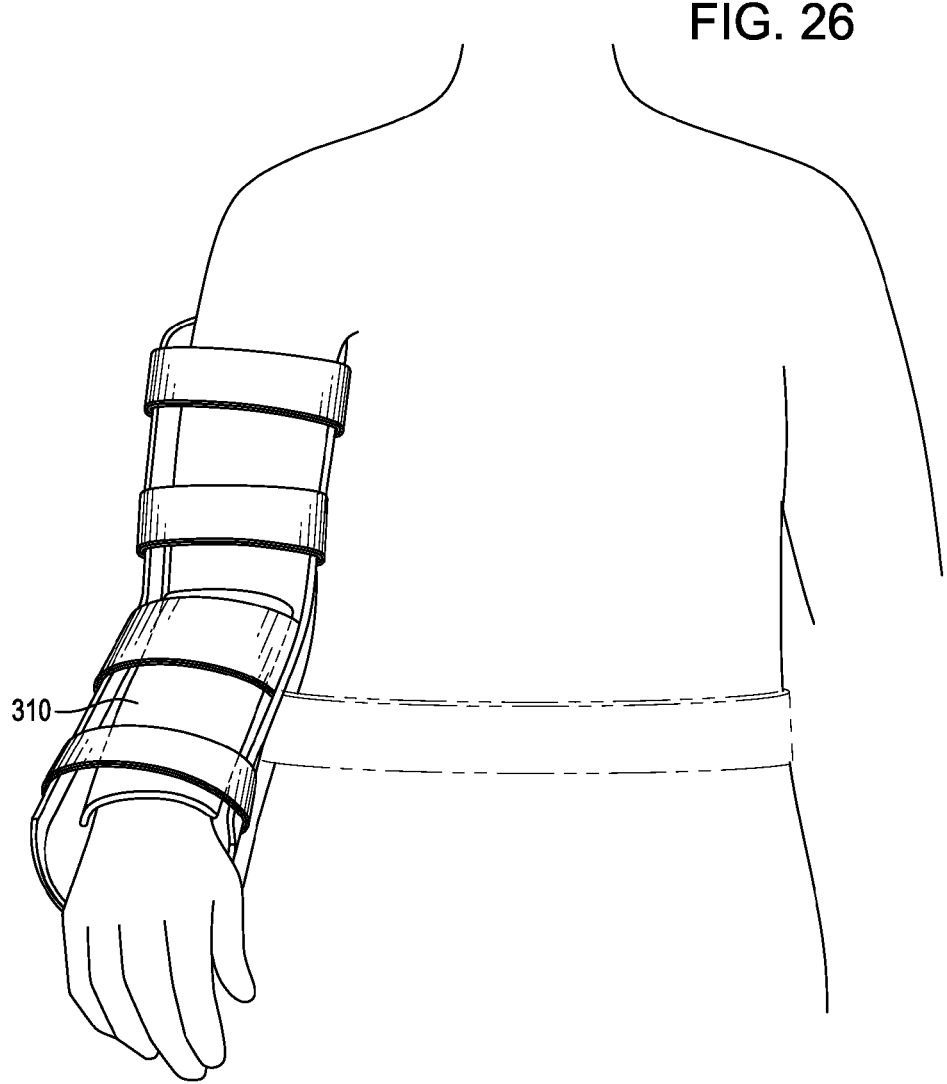

Another embodiment of a compression plate 310 for use on a forearm of a user is shown in FIGS. 25 and 26. The forearm compression plate 310 fits against a top portion of the forearm between the elbow joint and the wrist. Such a forearm compression plate 310 is used for radial and ulnar fractures. For distal radial fractures, the plate could extend over the wrist. The advantages of using such a compression plate with the arm support is that the compression plate 310 compresses the fracture site while the arm support 30 rigidly immobilizes the elbow and upper arm, thus preventing disruptive forces at the fracture site. Also, use of the arm support 30 and the compression plate 310 is more hygienic than the use of a cast because the compression plate is easily removable, allowing easy access for skincare. This advantage is provided by each of the embodiments over casts.

Figure 27:
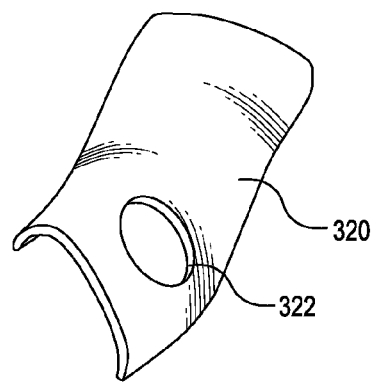
FIGS. 27 and 28 illustrate a thumb spica compression plate that includes an opening for receiving a thumb of a patient.
Figure 28:
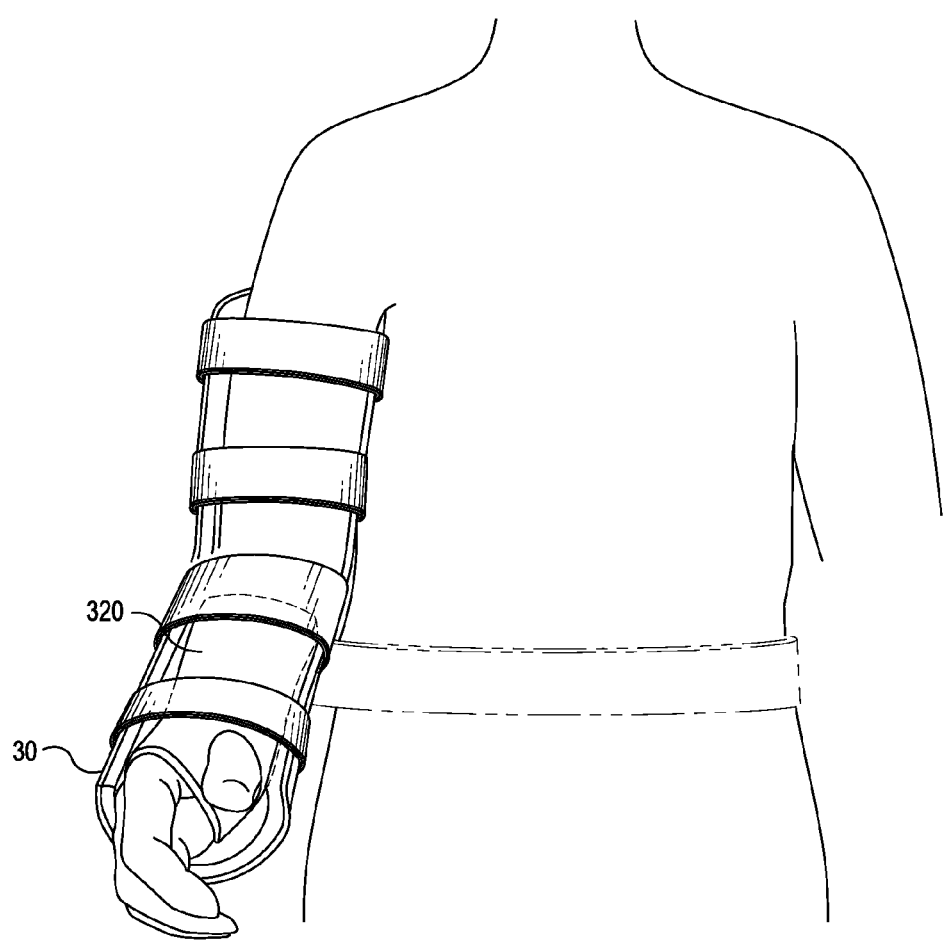

A third embodiment of a compression plate is shown in FIGS. 27 and 28, which illustrate a wrist compression plate 320 that includes an opening 322 for receiving a thumb of a patient. The wrist compression plate 320 is designed to fit over a portion of the forearm of the user and the base of the wrist, and to receive a thumb of the user through the opening 322. Such a compression plate 320 may be used for carpal fracture, such as the scaphoid. The advantages of using such a fracture plate are that it permits compression at the fracture site while the arm support 30 rigidly immobilizes the elbow and upper arm, thus preventing disruptive forces on the fracture site. The thumb opening 322 properly positions and stabilizes the wrist. The embodiment shown in FIG. 27 is designed to arrange the hand in a vertical manner; i.e., with the fingers stacked vertically when the forearm is supported by the arm support 30. Also, as described above, the use of the combined arm support 30 and the wrist compression plate 320 is more hygienic because it allows access to the skin for cleaning or other skincare.

Figure 29:
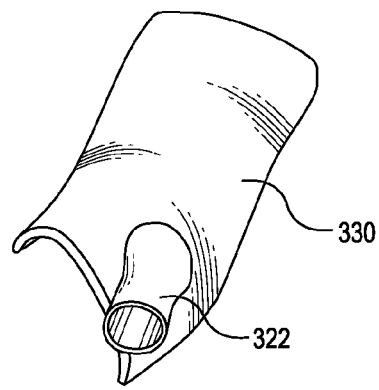
FIGS. 29 and 30 illustrate an alternate thumb spica compression plate.
Figure 30:
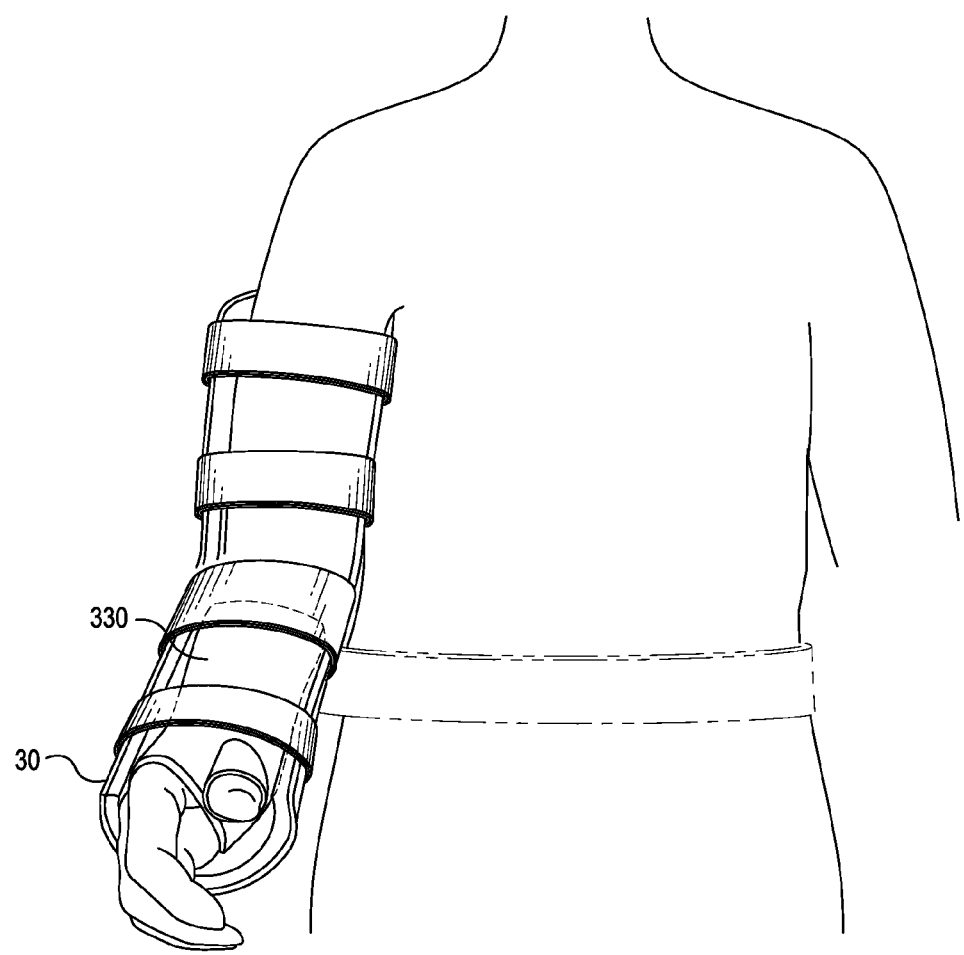

An alternate thumb spica compression plate 330 is shown in FIGS. 29 and 30. The thumb spica plate 330 also includes a spica 332 for receiving the base of a thumb. The embodiment shown in FIG. 29 is designed to arrange the hand in a vertical manner; i.e., with the fingers stacked vertically when the forearm is supported by the arm support 30. Presenting the arm in this manner is more of a spica type of support, with the compression plate 320 being more for supporting the wrist of the patient.

Figure 31:
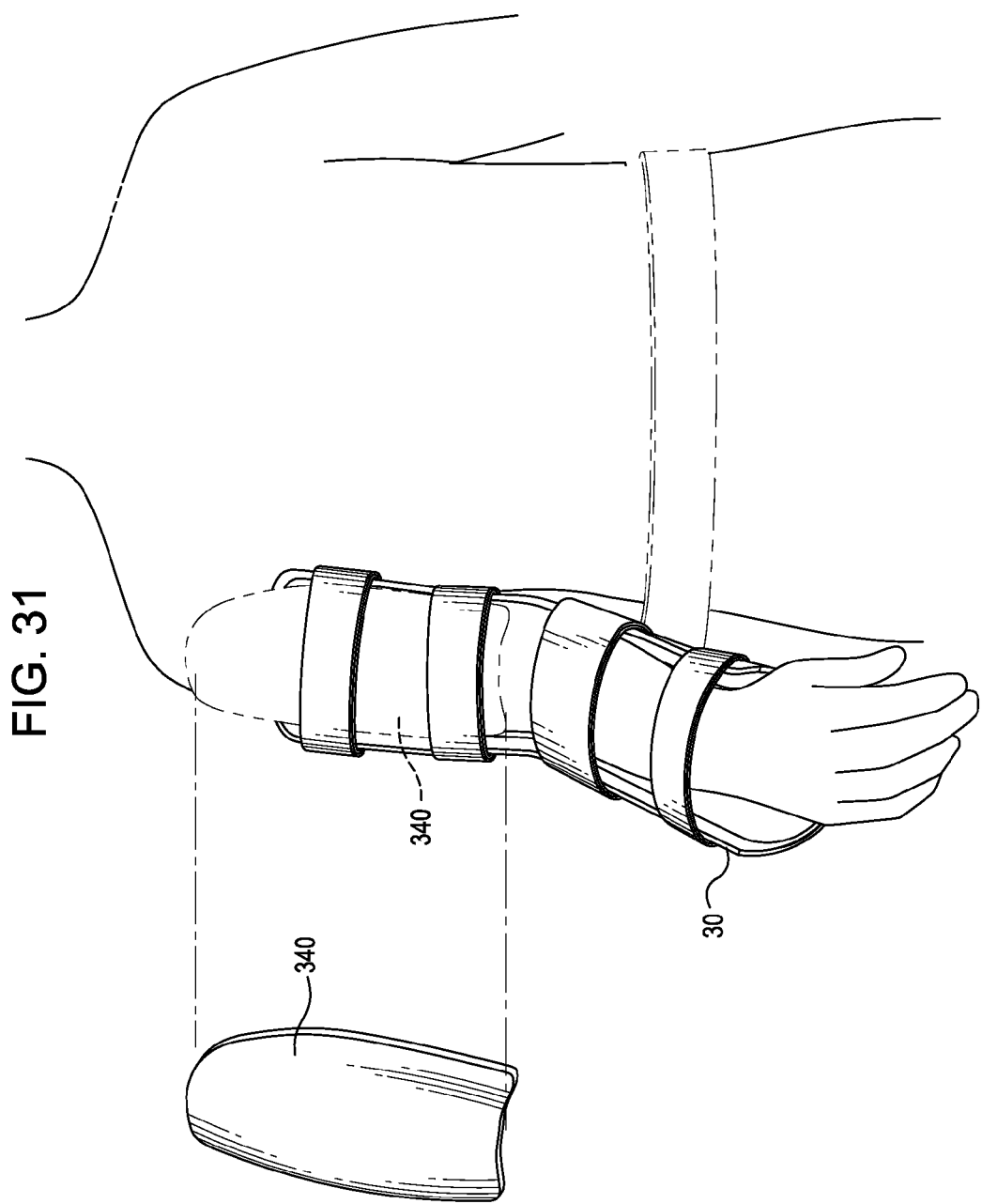
FIG. 31 shows a compression plate designed to fit against the upper arm, adjacent the bicep of a user.

Still another compression plate 340 is shown in FIG. 31. The compression plate 340 is designed to fit against the upper arm, adjacent the bicep of a user. Such a compression plate 340 is used for a humeral shaft fracture, particularly mid or distal humeral shaft fractures. An advantage to using such an upper arm compression plate 340 with the arm support 30 is that the combination provides compression around the fracture combined with the gravity alignment of the arm support to maintain bone alignment retention.

In embodiments, one or more of the features of the above described compression plate may be combined with other features of other compression plates to provide a desired compression arrangement for a patient. Moreover, more than one of the compression plates described above may be used for a single user in case of multiple fractures or when there is a need for additional support or compression. The compression plates may be supported by the straps described above with respect to the arm support 30. In addition, if needed, additional straps or other anchors may be provided for desired compression and alignment of the compression plate with the arm in the patient.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A fracture stabilization device, comprising:
   an arm support comprising:
   a rigid or semi-rigid lower forearm support configured to extend outward when the fracture stabilization device is worn by a patient, the forearm support comprising a receiving surface configured for receiving a forearm of the patient and supporting the forearm;
   a rigid or semi-rigid upper arm support for extending along a back portion of the patient's arm when worn by a patient; wherein the upper arm support comprises an opening on an anterior side of the upper arm support;
   a compression plate;
   a cold therapy system configured to conform to a shoulder portion of the arm; and wherein the cold therapy system comprises a tubing connector that is positionable at the opening; and
   a strap configured to hold the compression plate against a first portion of an arm of a patient, the first portion being opposite a second portion of the arm that is configured to be supported by the arm support, thereby applying a compressive force to the arm wherein the arm support is configured to be supported in a fixed position against the body of said patient;
   wherein the rigid or semi-rigid lower forearm support and the rigid or semi-rigid upper arm support are locked in place during use and configured to provide a fixed position for the patient's elbow.

* * * * *